(12) United States Patent
Kalnitsky et al.

(10) Patent No.: US 10,522,400 B2
(45) Date of Patent: Dec. 31, 2019

(54) EMBEDDED TEMPERATURE CONTROL SYSTEM FOR A BIOSENSOR

(71) Applicant: Taiwan Semiconductor Manufacturing Co., Ltd., Hsin-Chu (TW)

(72) Inventors: Alexander Kalnitsky, San Francisco, CA (US); Yi-Hsien Chang, Shetou Township (TW); Chun-Ren Cheng, Hsin-Chu (TW); Jui-Cheng Huang, Hsinchu (TW); Shih-Fen Huang, Jhubei (TW); Tung-Tsun Chen, Hsinchu (TW); Ching-Hui Lin, Taichung (TW)

(73) Assignee: Taiwan Semiconductor Manufacturing Co., Ltd., Hsin-Chu (TW)

( * ) Notice: Subject to any disclaimer, the term of this patent is extended or adjusted under 35 U.S.C. 154(b) by 270 days.

(21) Appl. No.: 15/216,853

(22) Filed: Jul. 22, 2016

(65) Prior Publication Data

US 2017/0343498 A1    Nov. 30, 2017

Related U.S. Application Data

(60) Provisional application No. 62/342,561, filed on May 27, 2016.

(51) Int. Cl.
*H01L 21/76* (2006.01)
*H01L 21/768* (2006.01)
*H01L 23/522* (2006.01)
*H01L 29/786* (2006.01)
*G01N 27/414* (2006.01)
(Continued)

(52) U.S. Cl.
CPC ... *H01L 21/76895* (2013.01); *G01N 27/4145* (2013.01); *H01L 23/345* (2013.01); *H01L 23/5228* (2013.01); *H01L 29/78696* (2013.01); *H01L 27/1203* (2013.01)

(58) Field of Classification Search
CPC .............. G01N 27/045; G01N 27/4145; H01L 21/76895; H01L 23/5228; H01L 29/78696
See application file for complete search history.

(56) References Cited

U.S. PATENT DOCUMENTS 5,369,246 A * 11/1994 Nanos .................... B32B 37/06
156/322
7,666,285 B1   2/2010 Cho
(Continued)

OTHER PUBLICATIONS

Final Office Action dated Aug. 12, 2016 U.S. Appl. No. 14/719,991.
(Continued)

*Primary Examiner* — Charles D Garber
*Assistant Examiner* — S M Sohel Imtiaz
(74) *Attorney, Agent, or Firm* — Eschweiler & Potashnik, LLC

(57) ABSTRACT

A biosensor with a heater embedded therein is provided. A semiconductor substrate comprises a source region and a drain region. The heater is under the semiconductor substrate. A sensing well is over the semiconductor substrate, laterally between the source region and the drain region. A sensing layer lines the sensing well. A method for manufacturing the biosensor is also provided.

20 Claims, 16 Drawing Sheets

(51) Int. Cl.
*H01L 23/34* (2006.01)
*H01L 27/12* (2006.01)

(56) References Cited

U.S. PATENT DOCUMENTS

| | | | |
|---|---|---|---|
| 7,728,401 | B2 | 6/2010 | Takatori |
| 8,405,169 | B2 | 3/2013 | Cheng et al. |
| 8,569,808 | B1 | 10/2013 | Chen et al. |
| 8,728,844 | B1 | 5/2014 | Liu et al. |
| 8,762,925 | B2 | 6/2014 | Chen et al. |
| 8,791,557 | B2 | 7/2014 | Chang et al. |
| 8,846,416 | B1 | 9/2014 | Chu et al. |
| 8,901,003 | B1* | 12/2014 | Pan .................. H01L 21/30625 216/88 |
| 9,528,939 | B2* | 12/2016 | Duer .................... G01N 21/553 |
| 2002/0017916 | A1* | 2/2002 | Costello ............ H01L 21/67109 324/750.09 |
| 2005/0123680 | A1 | 6/2005 | Kang |
| 2006/0057771 | A1* | 3/2006 | Kovacs .............. G01N 33/4836 438/106 |
| 2006/0197118 | A1 | 9/2006 | Migliorato et al. |
| 2007/0210350 | A1* | 9/2007 | Omura ................ H01L 23/4824 257/287 |
| 2007/0210807 | A1 | 9/2007 | Arisaka |
| 2008/0063566 | A1 | 3/2008 | Matsumoto |
| 2009/0065761 | A1* | 3/2009 | Chen .................. H01L 23/5256 257/5 |
| 2010/0230578 | A1 | 9/2010 | Horikoshi et al. |
| 2010/0248284 | A1 | 9/2010 | Chen |
| 2011/0209555 | A1* | 9/2011 | Ahles .................... B81B 3/0081 73/727 |
| 2011/0291673 | A1 | 12/2011 | Shibata |
| 2012/0021918 | A1 | 1/2012 | Bashir et al. |
| 2012/0032235 | A1 | 2/2012 | Bikumandla |
| 2013/0105868 | A1* | 5/2013 | Kalnitsky ............ G01N 27/414 257/288 |
| 2013/0200438 | A1* | 8/2013 | Liu ...................... G01N 27/414 257/253 |
| 2013/0256259 | A1 | 10/2013 | Chang et al. |
| 2013/0293878 | A1 | 11/2013 | Chang et al. |
| 2013/0307626 | A1* | 11/2013 | Mohammadi ....... H01L 21/0254 330/289 |
| 2013/0341734 | A1* | 12/2013 | Merz ..................... G01N 27/26 257/414 |
| 2014/0073039 | A1 | 3/2014 | Chang et al. |
| 2014/0134748 | A1 | 5/2014 | Liu et al. |
| 2014/0225166 | A1 | 8/2014 | Ellis-Monaghan et al. |
| 2014/0256030 | A1 | 9/2014 | Shen et al. |
| 2014/0264467 | A1* | 9/2014 | Cheng ................ G01N 27/4145 257/253 |
| 2014/0264468 | A1 | 9/2014 | Cheng et al. |
| 2014/0308752 | A1* | 10/2014 | Chang ................ G01N 27/4145 436/501 |
| 2014/0335640 | A1 | 11/2014 | Chang et al. |
| 2014/0370636 | A1 | 12/2014 | Dalton et al. |
| 2015/0129937 | A1* | 5/2015 | Chen .................. G01N 27/4145 257/253 |
| 2015/0330941 | A1 | 11/2015 | Smith |
| 2016/0209355 | A1 | 7/2016 | Chang et al. |
| 2017/0018626 | A1* | 1/2017 | Hoffman ........... H01L 29/66045 |

OTHER PUBLICATIONS

Petrucci, et al. "Thermal Characterization of Thin Film Heater for Lab-On-Chip Application." 2015 XVIII AISEM Annual Conference. Feb. 2015.
Nanohelix.net RealHelix qPCR Kit. Published in 2009. Retrieved online at http://www.nanohelix.net/02_products/view.asp?pack_code=277.
U.S. Appl. No. 15/386,545, filed Dec. 21, 2016.
Jang, et al. "Performance Enhancement of Capacitive-Coupling Dual-Gate Ion-Sensitive Field-Effect Transistor in Ultra-Thin-Body." Scientific Reports, 4: 5284. Published Jun. 13, 2014.
Romero-Garcia, et al.; "Silicon Nitride CMOS-compatible Platform for Integrated Photonics Applications at Visible Wavelengths;" Optics Express, vol. 21, No. 12, Jun. 17, 2013, p. 1-11.
Salm, et al. "Ultralocalized Thermal Reactions in Subnanoliter Droplets-in-air;" PNAS; vol. 110; No. 9; Feb. 26, 2013; p. 3310-3315.
"Supporting Information for Ultralocalized Thermal Reactions in Subnanoliter Droplets-in-air;" PNAS, vol. 110; No. 9, Feb. 26, 2013, p. 1-25.
Lee, et al.; "Microchip-based one step DNA Extraction and Real-Time PCR in one Chamber for Rapid Pathogen Identification;" Lab Chip; The Royal Society of Chemistry 2006; p. 886-895.
Dametto, Paolo; "DNA Amplification and Detection Using a pH-Sensing System: Implications for Current Analytical Technologies and Point-of-Care Nucleic Acid Tests;" Aug. 2013; p. 1-31.
Bhattacharya, et al.; "PCR-Based Detection in a Micro-Fabricated Platform;" Lab Chip; The Royal Society of Chemistry; 2008; p. 1130-1136.
Toumazou, et al. "Simultaneous DNA amplification and detection using a pH-sensing semiconductor system." Nature Methods, vol. 10, No. 7, Jul. 2013.
U.S. Appl. No. 13/480,161, filed May 24, 2012.
Mandavifar, et al. "Implementation of a Polysilicon Micro Electro-Thermal Detector in Gas Chromatography System with Applications in Portable Environmental Monitoring." ECS Journal of Solid State Science and Technology, 4 (10) S3062-S3066 (2015). Aug. 28, 2015.
Scorzoni, et al. "Thermal Characterization of a Thin Film Heater on Glass Substrate for Lab-on-Chip Applications." 2014 IEEE International Instrumentation and Measurement Technology Conference (I2MTC) Proceedings. May 12, 2014.
U.S. Appl. No. 14/719,991, filed May 22, 2015.
Non-Final Office Action dated Feb. 2, 2016 for U.S. Appl. No. 14/719,991.
U.S. Appl. No. 14/713,543, filed May 15, 2015.
Non-Final Office Action dated Jul. 18, 2016 for U.S. Appl. No. 14/713,543.
Non Final Office Action dated Sep. 6, 2016 U.S. Appl. No. 14/600,315.
Notice of Allowance dated Mar. 15, 2017 in connection with U.S. Appl. No. 14/600,315.
Notice of Allowance in connection with U.S. Appl. No. 14/719,991.
Final Office Action in connection with U.S. Appl. No. 14/719,991.
Non-Final Office Action in connection with U.S. Appl. No. 15/216,853.
Notice of Allowance in connection with U.S. Appl. No. 15/386,545.

* cited by examiner

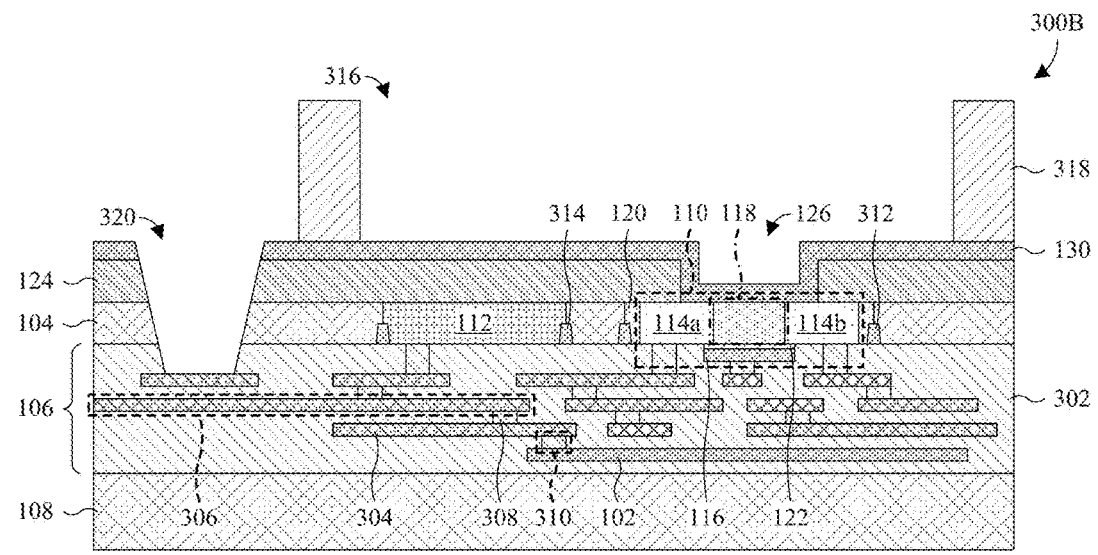
Fig. 3B
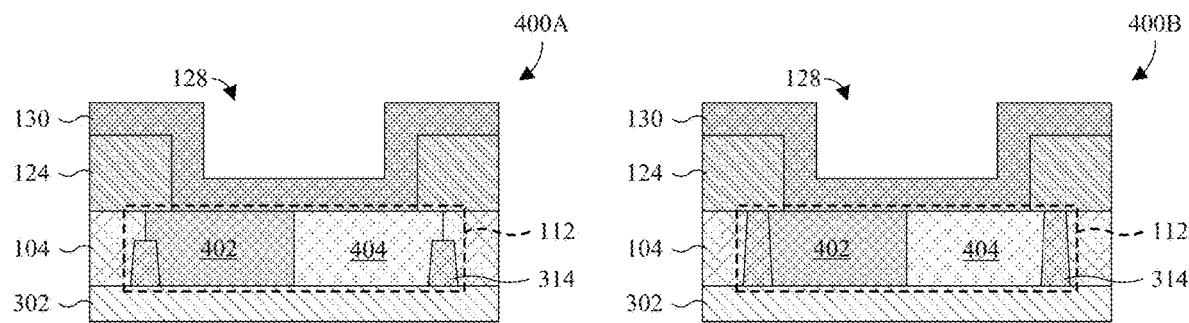
Fig. 4A             Fig. 4B

Fig. 5E   Fig. 5F

EMBEDDED TEMPERATURE CONTROL SYSTEM FOR A BIOSENSOR

REFERENCE TO RELATED APPLICATION

This Application claims the benefit of U.S. Provisional Application No. 62/342,561, filed on May 27, 2016, the contents of which are incorporated herein by reference in their entirety.

BACKGROUND

Biosensors are devices for sensing and detecting bio-entities, and typically operate on the basis of electronic, chemical, optical, or mechanical detection principles. Detection can be performed by detecting the bio-entities themselves, or through interaction and reaction between specified reactants and the bio-entities. Biosensors are widely used in different life-science applications, ranging from environmental monitoring and basic life science research to Point-of-Care (PoC) in-vitro molecular diagnostics.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIGS. 3A and 3B illustrate cross-sectional views of some more detailed embodiments of the biosensor of FIG. 1 respectively with and without a heating well.

FIGS. 4A-4F illustrate cross-sectional views of some more detailed embodiments of the biosensor of FIG. 1 respectively for different configurations and electrical isolation schemes of a temperature sensor.

FIGS. 5A-5F illustrate layout views of various embodiments of the heater in the biosensor of FIG. 1.

DETAILED DESCRIPTION

Figure 1:
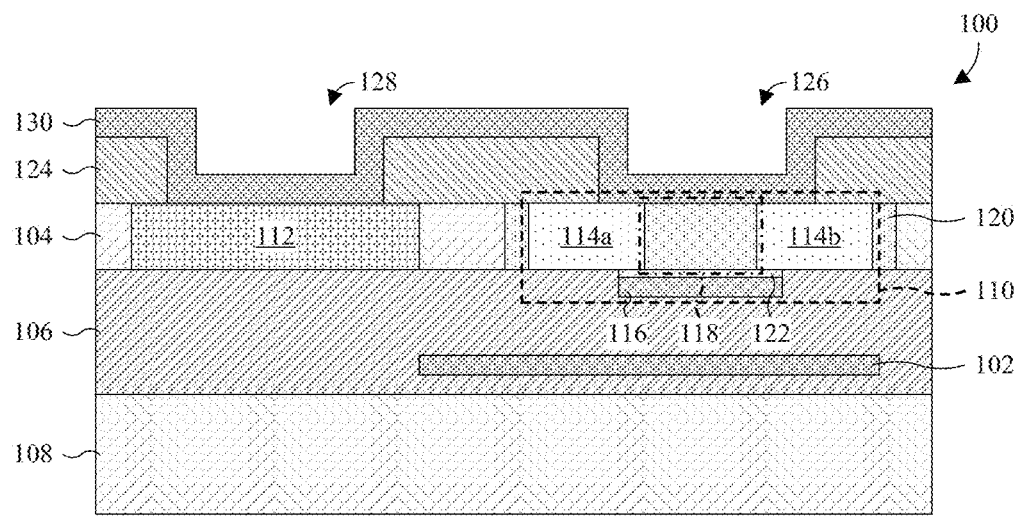
FIG. 1 illustrates a cross-sectional view of some embodiments of a biosensor with a biologically sensitive field-effect transistor (BioFET) and a heater.

The present disclosure provides many different embodiments, or examples, for implementing different features of this disclosure. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

One type of biosensor comprises a semiconductor substrate that is covered by a passivation layer and that accommodates a biologically sensitive field-effect transistor (BioFET). The BioFET comprises a source region and a drain region that are arranged within the semiconductor substrate and that define a channel region therebetween. Further, the BioFET comprises a gate arranged under the semiconductor substrate, laterally between the source region and the drain region. The passivation layer comprises a sensing well that exposes the semiconductor substrate, laterally between the source region and the drain region, and that is lined by a biosensing layer. The biosensing layer is configured to react with or bind to bio-entities to facilitate a change in the conductance of the channel region, such that the presence of the bio-entities may be detected based on the conductance of the channel region.

In operation, the bio-entities are suspended within a fluid and applied to the sensing well to detect the presence of the bio-entities. Further, before or after application of the fluid to the sensing well, the fluid may be heated to enhance the detection of the bio-entities. For example, the fluid may be heated during polymerase chain reaction (PCR). PCR is a technique for replicating a piece of DNA using thermal cycling and increases the number of pieces of DNA to a more readily detectable level. After the fluid is applied to the sensing well, pieces of DNA contact the biosensing layer and ions are released to vary a conductance of the channel region. As another example, the fluid may be heated during immunoassay. Immunoassay is a biochemical test that measures the presence or concentration of the analyte using an antibody or antigen that binds to the analyte. After the fluid is applied to the sensing well, the analyte binds to the biosensing layer. Subsequently, heat may be employed to improve an efficiency of an enzyme reaction in which ions are released to vary a conductance of the channel region.

To heat the fluid, a heating system external to the biosensor is employed. While the heating system may sufficiently heat the fluid, the heating system may suffer from a number of drawbacks since the heating system is external to the biosensor. For example, temperature control and uniformity may be poor. As another example, power consumption may be high and heating may be slow. As yet another example, high amounts of the fluid may be consumed due to evaporation over long heating times, thereby leading to high costs.

The present application is directed towards a biosensor with a heater embedded therein. In some embodiments, a semiconductor substrate comprises a source region and a drain region. The heater is under the semiconductor substrate. A sensing well is over the semiconductor substrate, laterally between the source region and the drain region. A biosensing layer lines the sensing well. In some embodiments, a back-end-of-line (BEOL) interconnect structure is arranged under the semiconductor substrate and accommodates the heater. Further, in some embodiments, a temperature sensor is laterally adjacent to the gate electrode and a controller controls the heater based on feedback from the temperature sensor.

Advantageously, the biosensor achieves good temperature control and uniformity due to the heater and, in some embodiments, the temperature sensor. For example, temperature control and uniformity may be good since the heater is embedded in the biosensor and close to the sensing well. As another example, temperature control and uniformity may be good since the temperature sensor may be used for closed loop temperature control. Further, heating is fast since to the heater is embedded in the biosensor and close to the sensing well. Even more, fluid consumption, power consumption, and costs are low since heating area is small.

With reference to FIG. 1, a cross-sectional view 100 of some embodiments of a biosensor with a heater 102 is provided. As illustrated, the heater 102 is arranged under a semiconductor substrate 104. In some embodiments, the heater 102 is part of a back-end-of-line (BEOL) interconnect structure 106 and/or is arranged over a carrier substrate 108. The carrier substrate 108 may be, for example, a bulk semiconductor substrate, such as a bulk substrate of monocrystalline silicon. Further, in some embodiments, the heater 102 has multiple zones that are individually controllable, and/or is titanium aluminum nitride, polysilicon, platinum, indium tin oxide, titanium nitride, or a combination of the foregoing. The semiconductor substrate 104 accommodates a BioFET 110 and may be, for example, a semiconductor layer of a semiconductor-on-insulator (SOI) substrate or a bulk semiconductor substrate.

The BioFET 110 is arranged on an underside of the semiconductor substrate 104 and, in some embodiments, is arranged laterally adjacent to a temperature sensor 112. The BioFET 110 comprises a pair of source/drain regions 114a, 114b and, in some embodiments, a gate electrode 116. The source/drains regions 114a, 114b have a first doping type and are arranged within the semiconductor substrate 104, respectively on opposite sides of a channel region 118 of the BioFET 110. The channel region 118 has a second doping type opposite the first doping and is arranged in the semiconductor substrate 104, laterally between the source/drain regions 114a, 114b. The first and second doping types may, for example, respectively be n-type and p-type, or vice versa. In some embodiments, the source/drain regions 114a, 114b and the channel region 118 are arranged within a well region 120 of the semiconductor substrate 104 that has the second doping type, and/or are electrically coupled to the BEOL interconnect structure 106. Further, in some embodiments, the source/drain regions 114a, 114b and the channel region 118 extend from a top surface of the semiconductor substrate 104 to a bottom surface of the semiconductor substrate 104. The gate electrode 116 is arranged under the semiconductor substrate 104, laterally between the source/drain regions 114a, 114b, and is spaced from the semiconductor substrate 104 by a gate dielectric layer 122 of the BioFET 110. In some embodiments, the gate electrode 116 is electrically coupled to the BEOL interconnect structure 106 and/or is metal, doped polysilicon, or a combination of the foregoing.

The temperature sensor 112 is configured to sense a temperature of a surrounding environment and may be, for example, used to generate feedback to control the heater 102. In some embodiments, the temperature sensor 112 comprises a first doped region (not shown) of the semiconductor substrate 104 and a second doped region (not shown) of the semiconductor substrate 104. The first and second doped regions respectively have the first and second doping types and contact one another to define a PN-junction. Further, the first and second doped regions may, for example, extend from the top surface of the semiconductor substrate 104 to the bottom surface of the semiconductor substrate 104. In other embodiments, the temperature sensor 112 is arranged under the semiconductor substrate 104 and comprises a layer of material (not shown) with a resistance that varies predictably in response to temperature variation, such as a layer of doped polysilicon layer. Further, in some embodiments, the temperature sensor 112 is electrically coupled to the BEOL interconnect structure 106.

A passivation layer 124 is arranged over the semiconductor substrate 104, and comprises a sensing well 126 and, in some embodiments, a heating well 128. The sensing well 126 extends into the passivation layer 124 to proximate the channel region 118 and is at least partially lined by a biosensing layer 130. Further, in some embodiments, the sensing well 126 extends through the passivation layer 124 to expose the channel region 118 and/or is arranged laterally between the source/drain regions 114a, 114b. The heating well 128 is arranged directly over the temperature sensor 112, laterally spaced from the sensing well 126, and extends into the passivation layer 124 to proximate the semiconductor substrate 104. Further, in some embodiments, the heating well 128 extends through the passivation layer 124 to expose the semiconductor substrate 104, and/or is at least partially lined by the biosensing layer 130. The passivation layer may be, for example, silicon dioxide, a buried oxide (BOX) layer of a SOI substrate, some other dielectric, or a combination of the foregoing.

The biosensing layer 130 lines the sensing well 126 and, in some embodiments, covers the passivation layer 124. Further, the biosensing layer 130 is configured to react with or bind to bio-entities to facilitate a change in the conductance of the channel region 118, such that the presence of the bio-entities may be detected based on the conductance of the channel region 118. The biosensing layer 130 may be, for example, titanium nitride, titanium, a high κ dielectric, some other material configured to react with or bind to the bio-entities, or a combination of the foregoing. A high κ dielectric is a dielectric with a dielectric constant κ that is greater than about 3.9. The bio-entities may be, for example, DNA, ribonucleic acid (RNA), drug molecules, enzymes, proteins, antibodies, antigens, or a combination of the foregoing. The biosensing layer 130 may, for example, also have a thickness of less than about 100 nanometers.

Advantageously, the heater 102 and, in some embodiments, the temperature sensor 112 promote good temperature control and uniformity. For example, temperature control and uniformity may be good since the heater 102 is embedded in the biosensor and close to the sensing well 126. As another example, temperature control and uniformity may be good since the temperature sensor 112 may provide feedback to control the heater 102 for closed loop temperature control. Further, power consumption is low and heating is fast since the heater 102 is embedded within the biosensor and close to the sensing well 126.

While the embodiments of FIG. 1 are illustrated with the heating well 128, it is to be appreciated that the heating well 128 may be omitted in other embodiments. Further, while the embodiments of FIG. 1 are illustrated with the gate electrode 116 and the gate dielectric layer 122, it is to be appreciated that the gate electrode 116 and the gate dielectric layer 122 may be omitted in other embodiments. Also, while the temperature sensor 112 is illustrated within the semiconductor substrate 104, the temperature sensor 112 may be omitted in other embodiments and/or may be arranged under the semiconductor substrate 104 in other embodiments. Even more, while the heater 102 is illustrated as being directly under the BioFET 110, the heater 102 may be arranged laterally adjacent to the BioFET 110 in other embodiments. Moreover, while the embodiments of FIG. 1 are described with the BioFET 110, the BioFET 110 may be replaced with some other type of transistor in other embodiments.

Figure 2A:
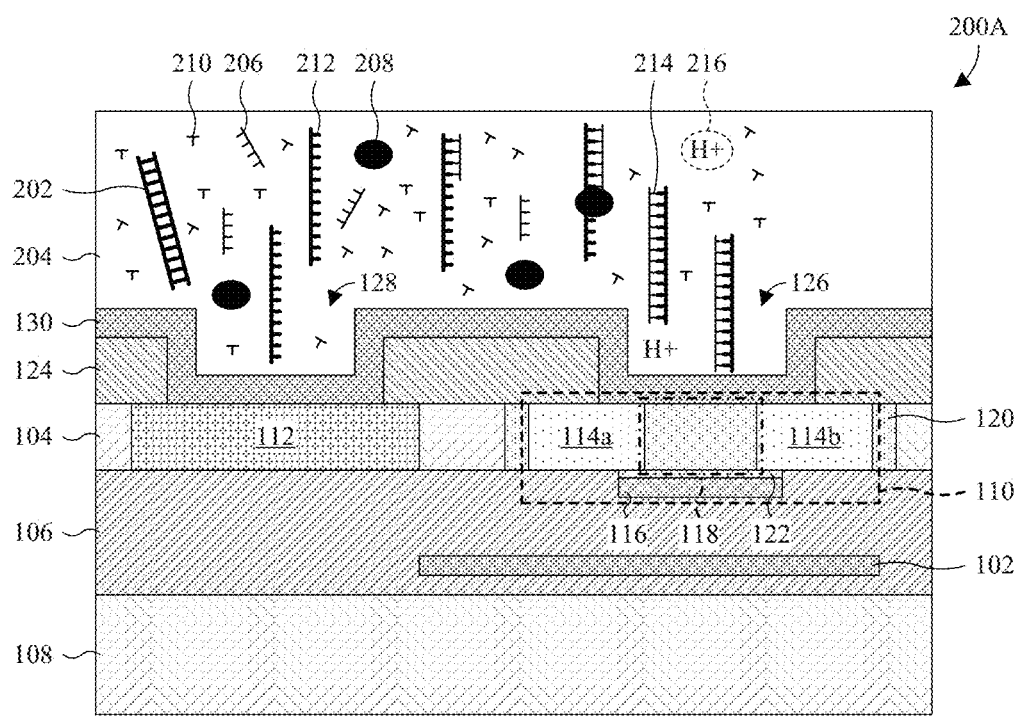
FIGS. 2A and 2B illustrate cross-sectional views of some embodiments of the biosensor of FIG. 1 during use respectively with polymerase chain reaction (PCR) and immunoassay.

With reference to FIG. 2A, a cross-sectional view 200A of some embodiments of the biosensor of FIG. 1 is provided to illustrate a process for using the biosensor with PCR to detect a DNA segment 202. As illustrated, the process progresses from left to right and begins by applying a fluid 204 to a top of the biosensor. The fluid 204 is an aqueous solution within which the DNA segment 202 may or may not be suspended. Further, primers 206, a polymerase 208, and deoxynucleoside triphosphates (dNTPs) 210 are suspended within the fluid 204. The primers 206 are complementary to DNA strands 212 of the DNA segment 202 and may be, for example, a hepatitis B virus (HBV) primer, a hepatitis C virus (HCV) primer, or a primer for the H1N1 (e.g., swine flu) or H5N1 (e.g., bird flu) subtypes of the influenza A virus.

With the fluid 204 applied to the biosensor, the heater 102 is employed to thermally cycle the fluid 204. To the extent that the DNA segment 202 is present in the fluid 204, the thermal cycling replicates the DNA segment 202 and increases the amount of DNA segments to a more readily detectable level. Further, the thermal cycling comprises multiple thermal cycles, each thermal cycle heating and cooling the fluid 204 and each thermal cycle doubling the amount of DNA segments present in the fluid 204. In some embodiments, the thermal cycling comprises about 20-40 thermal cycles, such as about 20 thermal cycles.

A first thermal cycle comprises heating the fluid 204 to break apart the DNA strands 212 of the DNA segment 202. For example, the fluid 204 may be heated to a temperature of about 90-100 degrees Celsius (° C.), such as about 94-98° C., for about 1-9 seconds, such as about 3 or 4 seconds. The temperature of the fluid 204 is then lowered to allow the primers 206 to bind to the DNA strands 212. For example, the temperature of the fluid 204 may be lowered to about 50-65° C., such as about 56-58° C., for about 1-9 seconds, such as about 3 or 4 seconds. Thereafter, the temperature of the fluid 204 is changed to an activity temperature of the polymerase 208 to synthesize new DNA segments 214 using the dNTPs 210. For example, the temperature of the fluid 204 may be changed to between about 75-80° C., such about 72° C. The duration with which the fluid 204 is held at the activity temperature varies depending upon the polymerase 208 and the length of the DNA strands 212, but may be, for example, about 120 seconds, such as about 110-112 seconds.

Subsequent to the first thermal cycle, one or more additional thermal cycles are performed to continue increasing the amount of DNA segments. With each additional thermal cycle, the new DNA segments of the previous thermal cycle are replicated as done for the DNA segment 202 in the first thermal cycle, such that the amount of DNA segments increases exponentially. Further, subsequent to the first thermal cycle, the conductance of the channel region 118 of the BioFET 110 is measured to identify the presence of DNA segments and, in some embodiments, the amount of DNA segments since the conductance of the channel region 118 varies based on the amount of DNA segments in the fluid 204. When a DNA segment lands on the biosensing layer 130, the DNA segment binds to the biosensing layer 130 and releases a hydrogen ion 216 into the fluid 204. The hydrogen ion 216, in turn, increases the pH of the fluid 204 and varies the conductance of the channel region 118. Therefore, as the amount of DNA segments increases, the pH of the fluid 204 increases and the extent of the change in the conductance of the channel region 118 increases.

For qualitative PCR, the conductance of the channel region 118 is measured after performing the one or more additional thermal cycles and is compared to the conductance of the channel region 118 before the first thermal cycle. To the extent the conductance varies by a threshold amount, the DNA segment 202 is present in the fluid 204. Otherwise, the DNA segment 202 is not present in the fluid 204.

For quantitative or real-time PCR, the conductance of the channel region 118 is measured after performing each thermal cycle. To the extent that the measurements are substantially the same, the DNA segment 202 is not present in the fluid 204. Otherwise, the measurements are graphed in a Cartesian coordinate system in which the abscissa is thermal cycle number and the ordinate is conductance. Further, a curve is fit to the measurements and is matched to curves for known amounts of DNA segments. The curve may be fit to the measurements by, for example, polynomial regression, and/or may be, for example, a sigmoid curve or a logistic curve. Thereafter, based on the matching, the amount of DNA segments in the fluid 204 is identified as the amount for the closest matching curve.

Advantageously, the heater 102 and, in some embodiments, the temperature sensor 112 promote good temperature control and uniformity. Further, power consumption is low and heating is fast. Even more, low amounts of the fluid 204 are consumed and costs are low since the thermal cycling time is short.

Figure 2B:
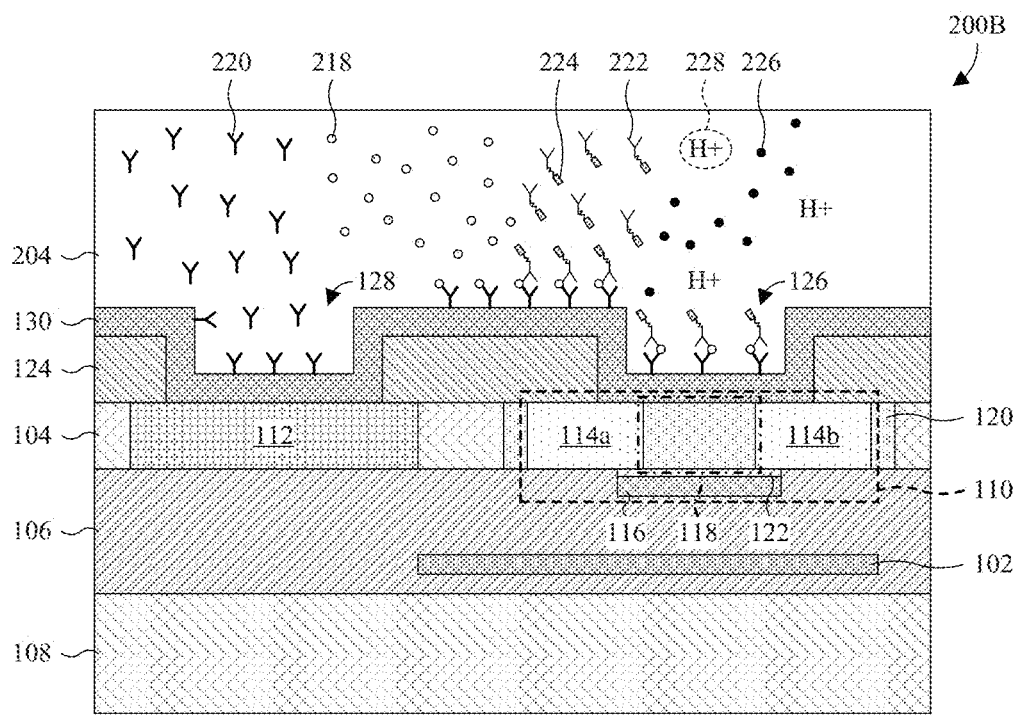

With reference to FIG. 2B, a cross-sectional view 200B of some embodiments of the biosensor of FIG. 1 is provided to illustrate a process for using the biosensor with immunoassay to detect antigens 218. As illustrated, the process progresses from left to right and begins by applying a fluid 204 to a top of the biosensor. The fluid 204 is an aqueous solution within which first antibodies (capture antibodies) 220 are suspended. When first antibodies contact the biosensing layer 130, the first antibodies bind to the biosensing layer 130. Subsequently, first antibodies unbound to the biosensing layer 130 are washed away or removed from the fluid 204.

A test sample which may or may not contain the antigens 218 is next added to the fluid 204. The antigens 218 are complementary to the first antibodies 220, such that antigens contacting the first antibodies 220 bind to the first antibodies 220. After applying the test sample, unbound antigens are washed away or removed from the fluid 204. Further, second antibodies (detection antibodies) 222 bound to reporter enzymes 224 are added to the fluid 204. The second antibodies 222 are complementary to the antigens 218, such that second antibodies contacting the antigens 218 bind to the antigens 218. The reporter enzymes 224 may be, for example, alkaline phosphatase (ALP) or horseradish peroxidase (HRP). Thereafter, unbound second antibodies are washed away or removed from the fluid 204, such that the second antibodies 222 only remain if the fluid 204 contains the antigens 218.

Chemical substrates 226 are added to the fluid 204 in the presence of heat from the heater 102. The chemical substrates 226 may be, for example, ascorbic acid 2-phasphate (AA-P). To the extent that the second antibodies 222 remain, the chemical substrates 226 react with the reporter enzymes 224 to release hydrogen ions 228 into the fluid 204. The heater 102 advantageously improves the efficiency of the reaction. The hydrogen ions 216, in turn, increase the pH of the fluid 204 and vary the conductance of the channel region 118, thereby allowing the antigens 218 to be detected. For example, the conductance of the channel region 118 may be measured before and after adding the chemical substrates 226 to the fluid 204. To the extent the conductance varies by a threshold amount, the antigens 218 are present in the fluid 204. Otherwise, the antigens 218 are not present in the fluid 204.

Figure 3A:
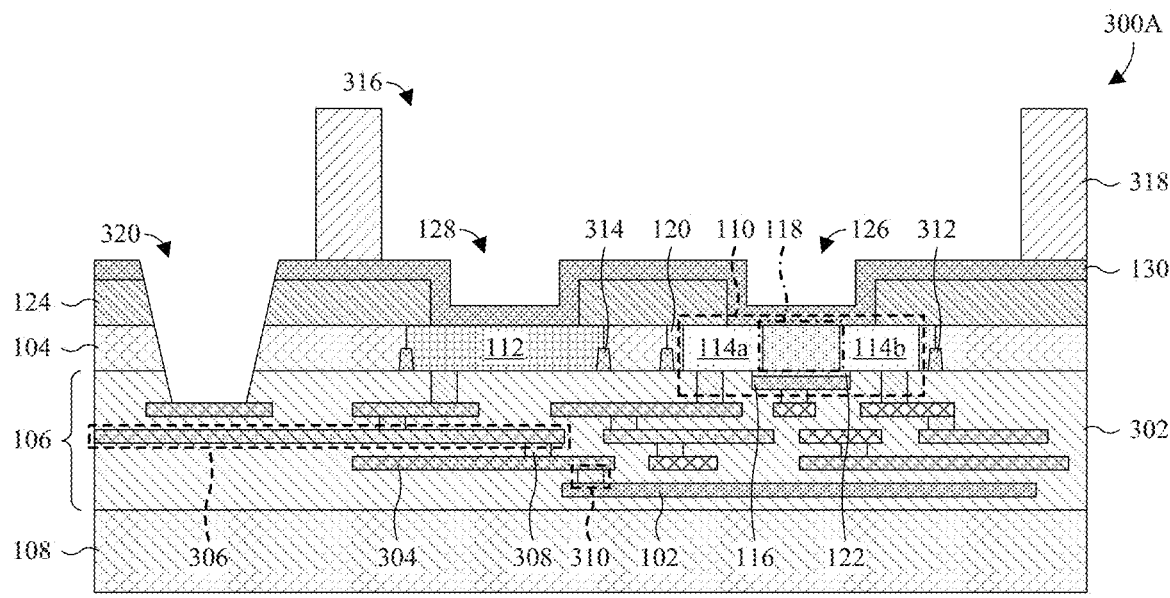

With reference to FIG. 3A, a cross-sectional view 300A of some more detailed embodiments of the biosensor of FIG. 1 is provided. As illustrated, a BEOL interconnect structure 106 is arranged under a semiconductor substrate 104, between the semiconductor substrate 104 and a carrier substrate 108. The BEOL interconnect structure 106 comprises an interlayer dielectric (ILD) layer 302 within which first interconnect layers 304 of line or pad features 306 and second interconnect layers 308 of via features 310 are alternatingly stacked. The ILD layer 302 may be, for example, silicon dioxide, silicon nitride, a low κ dielectric, some other dielectric, or a multi-layer film comprising a combination of the foregoing. As used herein, a low-κ dielectric is a dielectric with a dielectric constant κ less than about 3.9.

The first interconnect layers 304 electrically couple the second interconnect layers 308 together, and the second interconnect layers 308 electrically couple the first interconnect layers 304 together. For example, each neighboring pair of first interconnect layers may be electrically coupled by a second interconnect layer arranged therebetween, and/or each neighboring pair of second interconnect layers may be electrically coupled by a first interconnect layer arranged therebetween. Further, the first and second interconnect layers 304, 308 electrically couple to a heater 102 arranged in the ILD layer 302, a BioFET 110 arranged in the semiconductor substrate 104, a temperature sensor 112 arranged laterally adjacent to the BioFET 110, or a combination of the foregoing. The first and second interconnect layers 304, 308 may be, for example, copper, aluminum copper, aluminum, tungsten, some other conductive material, or a combination of the foregoing.

The BioFET 110 and, in some embodiments, the temperature sensor 112 are arranged in the semiconductor substrate 104. For example, the temperature sensor 112 may be a PN diode that is arranged in the semiconductor substrate 104. Further, in some embodiments, a first isolation region 312 is arranged in the semiconductor substrate 104 to electrically isolate the BioFET 110, and/or a second isolation region 314 is arranged in the semiconductor substrate 104 to electrically isolate the temperature sensor 112. The first isolation region 312 extends vertically into the semiconductor substrate 104 and extends laterally to enclose the BioFET 110 and/or a well region 120 within which the BioFET 110 is arranged. Similarly, the second isolation region 314 extends vertically into the semiconductor substrate 104 and extends laterally to enclose the temperature sensor 112. The first and/or second isolation regions 312, 314 may be, for example, shallow trench isolation (STI) regions. Further, the first and/or second isolation regions 312, 314 may, for example, extend from a bottom surface of the semiconductor substrate 104 to a top surface of the semiconductor substrate 104.

A passivation layer 124 is arranged over the semiconductor substrate 104, and comprises a sensing well 126 and a heating well 128 respectively arranged over the BioFET 110 and the temperature sensor 112. The sensing well 126 and the heating well 128 are lined by a biosensing layer 130 and are covered by a fluidic channel 316. The fluidic channel 316 may, for example, be defined laterally between a channel structure 318 arranged over the passivation layer 124. The passivation layer 124 also accommodates a pad opening 320 arranged laterally adjacent to the temperature sensor 112, on an opposite side of the temperature sensor 112 as the BioFET 110. The pad opening 320 extends into the ILD layer 302, through the passivation layer 124 and the semiconductor substrate 104, to expose one of the line or pad features 306 of the first interconnect layers 304. Further, in some embodiments, the pad opening 320 extends through the biosensing layer 130.

With reference to FIG. 3B, a cross-sectional view 300B of some more detailed embodiments of the biosensor of FIG. 1 is provided. As illustrated, FIG. 3B is a variant of FIG. 3A in which the heating well 128 of FIG. 3A is omitted. The heating well 128 of FIG. 3A may, for example, be omitted in situations where the passivation layer 124 is sufficiently thin and/or the temperature sensor 112 is sufficiently sensitive to allow the temperature sensor 112 to efficiently measure the temperature of fluid arranged thereover in the fluidic channel 316. Further, while FIG. 3B was illustrated with the temperature sensor 112, the temperature sensor 112 may also be omitted in other embodiments.

With reference to FIGS. 4A-4F, cross-sectional views 400A-400F of some more detailed embodiments of the biosensor of FIG. 1 are provided to illustrated different configurations and electrical isolation schemes for the temperature sensor 112 of FIG. 1. The various embodiments may, for example, also find application in FIGS. 3A and 3B.

As illustrated by the cross-sectional view 400A of FIG. 4A, the temperature sensor 112 comprises a first doped region 402 and a second doped region 404 both arranged in the semiconductor substrate 104. The first and second doped regions 402, 404 have opposite doping types and contact one another to define a PN-junction. For example, the first doped region 402 may be p-type and the second doped region 404 may be n-type, or vice versa. Further, in some embodiments, the first and second doped regions 402, 404 extend through the semiconductor substrate 104, from a bottom surface of the semiconductor substrate 104 to a top surface of the semiconductor substrate 104. Advantageously, the temperature sensor 112 may measure temperature with accuracy within 1° C. of the true temperature.

Also illustrated by the cross-sectional view 400A of FIG. 4A, an isolation region 314 is arranged in the semiconductor substrate 104 to electrically isolate the temperature sensor 112 from a surrounding environment. The isolation region 314 extends vertically into the semiconductor substrate 104, from the bottom surface of the semiconductor substrate 104, and terminates at a location spaced below the top surface of the semiconductor substrate 104. Further, in some embodiments, the isolation region 314 extends laterally to enclose the temperature sensor 112.

As illustrated by the cross-sectional view 400B of FIG. 4B, alternative embodiments of FIG. 4A are provided in which the isolation region 314 extends through the semiconductor substrate 104, from a bottom surface of the semiconductor substrate 104 to a top surface of the semiconductor substrate 104.

Figure 4C:
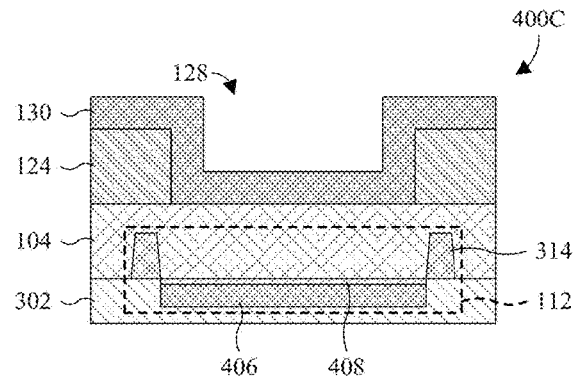
Figure 4D:
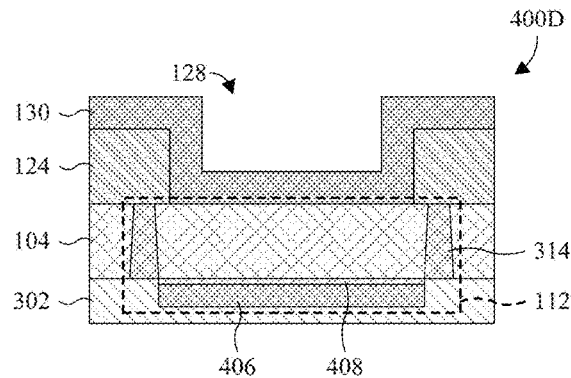

As illustrated by the cross-sectional views 400C, 400D of FIGS. 4C and 4D, alternative embodiments respectively of FIGS. 4A and 4B are provided in which the temperature sensor 112 comprises a temperature sensing layer 406 arranged under the semiconductor substrate 104. The temperature sensing layer 406 has a resistance that varies with temperature, such that ambient temperature may be measured by measuring the resistance of the temperature sensing layer 406. The temperature sensing layer 406 may be, for example, polysilicon or some other material with a resistance that varies based on temperature. Further, in some embodiments, the temperature sensing layer 406 is electrically isolated from the semiconductor substrate 104 by a temperature dielectric layer 408 arranged between the semiconductor substrate 104 and the temperature sensing layer 406.

Figure 4E:
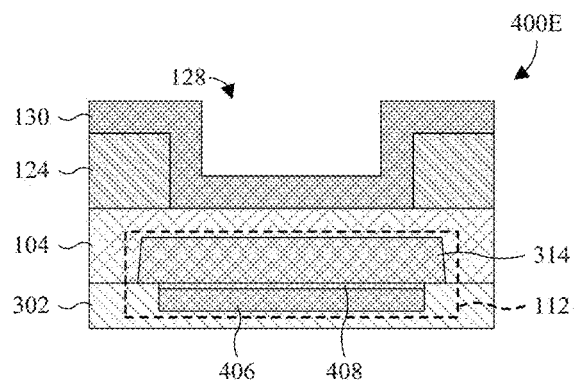
Figure 4F:
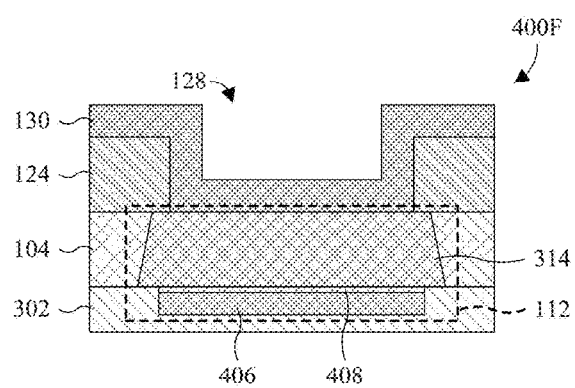

As illustrated by the cross-sectional views 400E, 400F of FIGS. 4E and 4F, alternative embodiments respectively of FIGS. 4C and 4D are provided in which the isolation region 314 extends from one side of the temperature sensing layer 406 to an opposite side of the temperature sensing layer 406 to cover the temperature sensing layer 406. Further, in some embodiments, the temperature dielectric layer 408 is omitted.

While the various embodiments of FIGS. 4A-4F include a heating well 128 over the temperature sensor 112, the heating well 128 may be omitted in other embodiments. Similarly, while the various embodiments of FIGS. 4A-4F include the isolation region 314, the isolation region 314 may be omitted in other embodiments.

With reference to FIGS. 5A-5F, layout views 500A-500E of various embodiments of the heater 102 of FIG. 1 are provided. The various embodiments may, for example, also find application in FIGS. 3A and 3B.

Figure 5A:
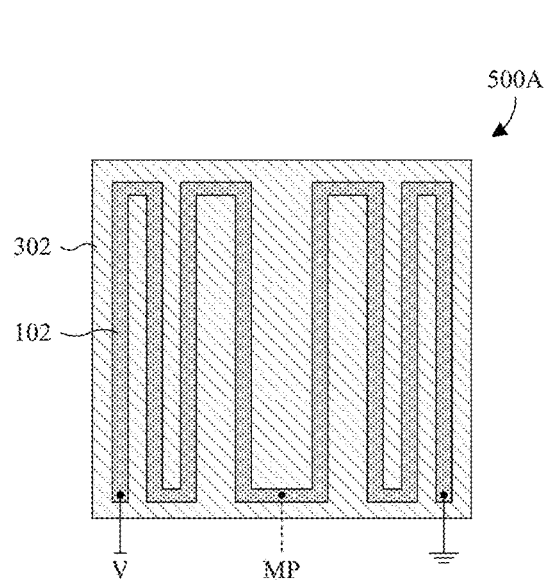

As illustrated by the layout view 500A of FIG. 5A, the heater 102 meanders back and forth from a first end of the heater 102 to a second end of the heater 102 that is opposite the first end. In some embodiments, the heater 102 has the shape of a square or sine wave with a frequency that decreases from the first end of the heater 102 to a midpoint MP of the heater 102, and that increases from the midpoint of the heater 102 to the second end of the heater 102. Further, in some embodiments, the heater 102 is symmetrical about the midpoint MP. The heater 102 may be, for example, titanium aluminum nitride, polysilicon, platinum, indium tin oxide, titanium nitride, or a combination of the foregoing.

In operation, the heater 102 resistively generates heat upon application of a heating voltage V across the first and second ends of the heater 102. The heating voltage V may be varied to vary the current flowing through the heater 102 and/or the power applied to the heater 102, such that the amount of heat generated by the heater 102 may be varied. Further, the shape of the heater 102 may be varied to control the distribution of generated heat.

Figure 5B:
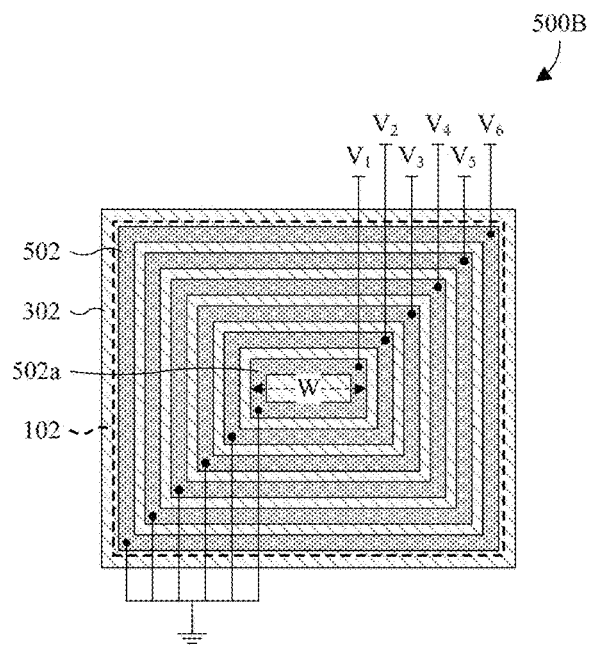

As illustrated by the layout view 500B of FIG. 5B, the heater 102 comprises N heating segments 502, where N is greater than 1. For example, N may be 6 or 7. The N heating segments 502 are rectangle-ring shaped or square-ring shaped, and increase in width W from a first heating segment 502a to an Nth heating segment. Further, except for the first heating segment 502a, each heating segment n extends laterally to enclose the (n−1)th heating segment. In some embodiments, centroids of the N heating segments 502 are aligned and/or the heater 102 is symmetrical about the aligned centroids of the N heating segments 502. The N heating segments 502 may be, for example, titanium aluminum nitride, polysilicon, platinum, indium tin oxide, titanium nitride, or a combination of the foregoing.

In operation, the N heating segments 502 resistively generate heat upon application of heating voltages $V_1$, $V_2$, $V_3$, $V_4$, $V_5$, $V_6$ respectively across the N heating segments 502. The heating voltages $V_1$, $V_2$, $V_3$, $V_4$, $V_5$, $V_6$ may be varied to vary the amount of current flowing through the N heating segments 502 and/or the power applied to the N heating segments 502, thereby varying the amount of heat generated by the N heating segments 502. Further, the heating voltages $V_1$, $V_2$, $V_3$, $V_4$, $V_5$, $V_6$ may be varied such that the power applied to the N heating segments 502 and/or the current flowing through the N heating segments 502 is the same or different. In some embodiments, the N heating segments 502 are individually controllable heating zones and/or are grouped into multiple individually controllable heating zones. For example, the heating voltages $V_1$, $V_2$, $V_3$, $V_4$, $V_5$, $V_6$ may be individually controllable or may be grouped into multiple individually controllable groups.

Figure 5C:
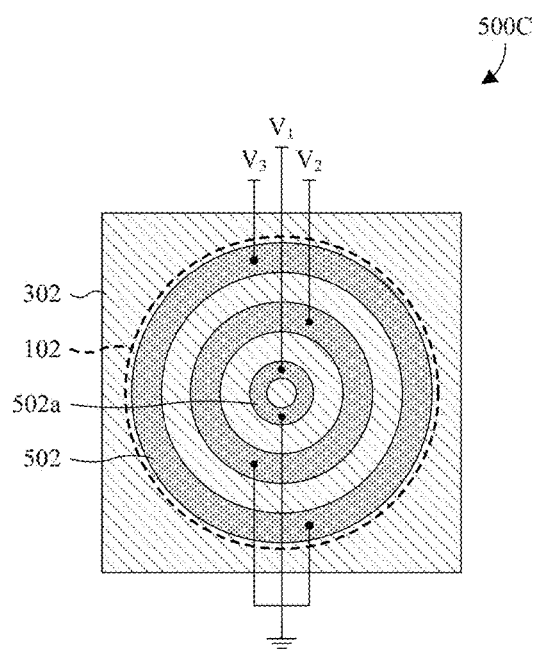

As illustrated by the layout view 500C of FIG. 5C, alternative embodiments of FIG. 5B are provided in which the N heating segments 502 are ring shaped.

Figure 5D:
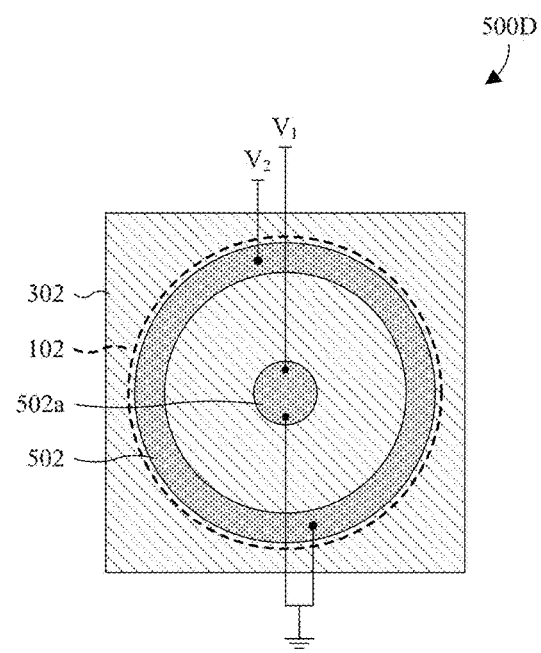

As illustrated by the layout view 500D of FIG. 5D, alternative embodiments of FIG. 5C are provided in which the first heating segment 502a is a circle.

As illustrated by the layout view 500E of FIG. 5E, alternative embodiments of FIG. 5B are provided in which the N heating segments 502 are line shaped. The N heating segments 502 extend in parallel in a first direction and are laterally spaced in a second direction that is parallel to the first direction. Along the second direction, the N heating segments 502 decrease in thickness T from a first end of the heater 102 to a midpoint MP of the heater 102 and increase in thickness T from the midpoint of the heater 102 to a second end of the heater 102. In some embodiments, the heater 102 is symmetrical about the midpoint MP. Along the first direction, a heating voltage V may be applied across the N heating segments 502 to resistively generate heat. In alternative embodiments, individual heating voltages are applied across the N heating segments 502 in the first direction.

As illustrated by the layout view 500F of FIG. 5F, alternative embodiments of FIG. 5E are provided in which the N heating segments 502 have the same thickness T.

Figure 6:
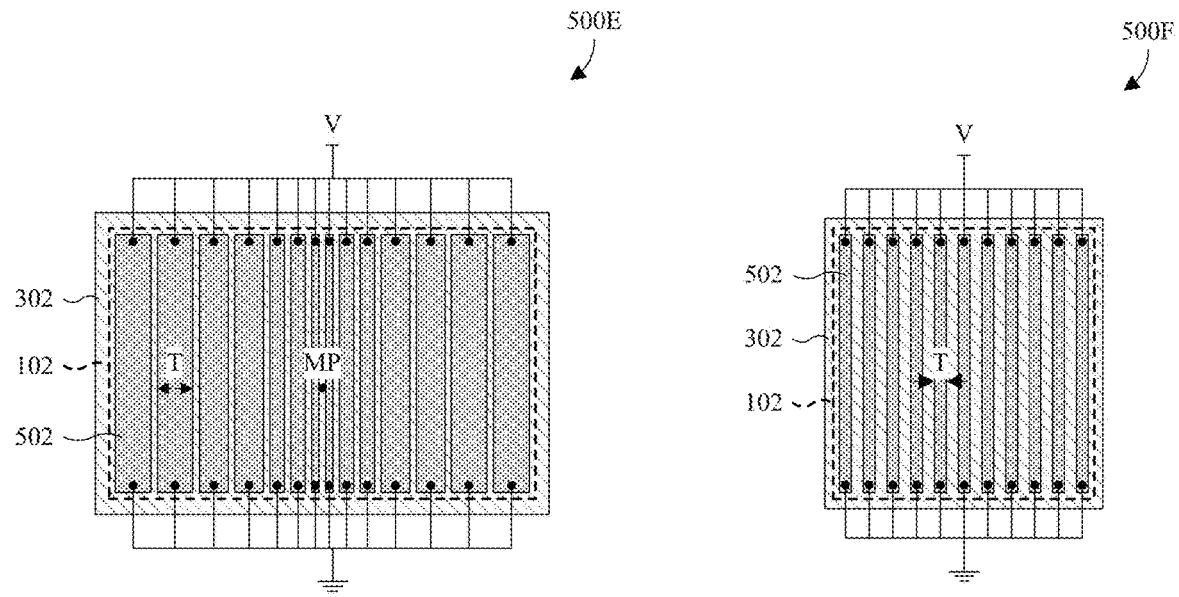
FIG. 6 illustrates a circuit diagram of some embodiments of a biosensor with an array of unit cells each having a BioFET and a heater.
Figure 6:
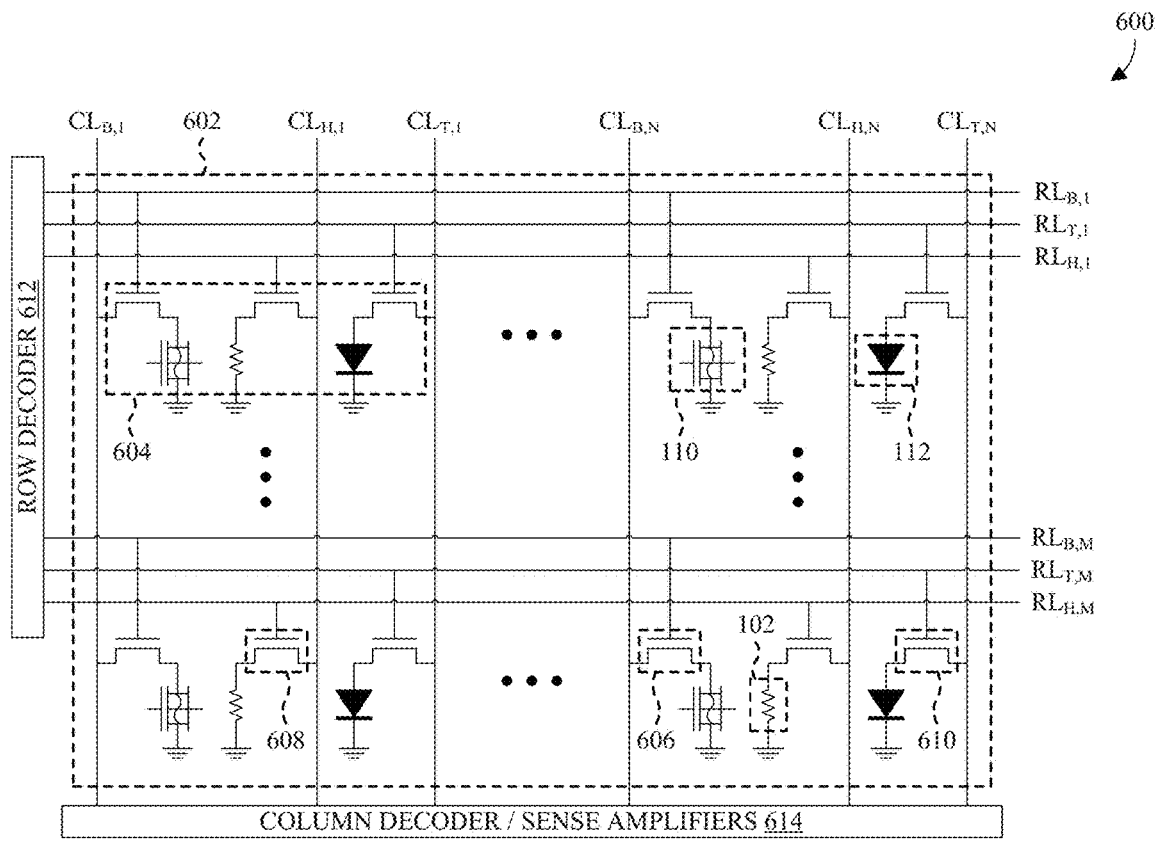

With reference to FIG. 6, a circuit diagram 600 of some embodiments of a biosensor with an array 602 of unit cells 604 is provided. As illustrated, the unit cells 604 are arranged in M rows and N columns, where M and N are each greater than 0. For example, M and N may each be 2. For each row, unit cells of the row are electrically coupled to row lines $RL_{B,1}$, $RL_{T,1}$, $RL_{H,1}$, $RL_{B,M}$, $RL_{T,M}$, $RL_{H,M}$ shared by the unit cells of the row. For each column, unit cells of the column are electrically coupled to column lines $CL_{B,1}$, $CL_{T,1}$, $CL_{H,1}$, $CL_{B,N}$, $CL_{T,N}$, $CL_{H,N}$ shared by the unit cells of the column. Such a configuration may, for example, be similar to that used with an array of dynamic random-access memory (DRAM) cells.

The unit cells 604 comprise respective BioFETs 110 and respective heaters 102. The BioFETs 110 are configured to sense the presence and/or concentration of bio-entities in a fluid. Further, the BioFETs 110 are selectively coupled electrically to respective column lines $CL_{B,1}$, $CL_{B,N}$ by respective BioFET access transistors 606 that are gated by respective row lines $RL_{B,1}$, $RL_{B,M}$. The heaters 102 are configured to heat the fluid to facilitate sensing and may, for example, have one of the layouts of FIGS. 5A-5F. Further, in some embodiments, the heaters 102 are selectively coupled electrically to respective column lines $CL_{H,1}$, $CL_{H,N}$ by respective heater access transistors 608 that are gated by respective row lines $RL_{H,1}$, $RL_{H,M}$. Where the heaters 102 individually comprise multiple heating segments or zones, the heaters 102 may, for example, be individually associated with multiple heater access transistors (one for each heating segments or zone), multiple row lines corresponding to the multiple heater access transistors, and multiple column lines corresponding to the multiple heater access transistors. In some embodiments, the unit cells 604 further comprise respective temperature sensors 112 configured to measure the temperature of the fluid and to provide feedback for control of the heaters 102. The temperature sensors 112 may, for example, have one of the configurations of FIGS. 4A-4F. Further, the temperature sensors 112 may, for example, be selectively coupled electrically to respective column lines $CL_{T,1}$, $CL_{T,N}$ by respective temperature access transistors 610 that are gated by respective row lines $RL_{T,1}$, $RL_{T,M}$. The unit cells 604 may, for example, be individually configured as described with regard to FIG. 1, FIG. 3A, or FIG. 3B.

The row lines $RL_{B,1}$, $RL_{T,1}$, $RL_{H,1}$, $RL_{B,M}$, $RL_{T,M}$, $RL_{H,M}$ are electrically coupled a row decoder 612, and the column lines $CL_{B,1}$, $CL_{T,1}$, $CL_{H,1}$, $CL_{B,N}$, $CL_{T,N}$, $CL_{H,N}$ are electrically coupled to a column decoder/sense amplifier 614. The row decoder 612 is configured to select a row of unit cells to read out measurements by respective temperature sensors and/or respective BioFETs, and/or to drive respective heaters. The column decoder/sense amplifier 614 is configured to select a column of unit cells to read out measurements by respective temperature sensors and/or respective BioFETs, and/or to drive respective heaters. Further, the column decoder/sense amplifier 614 is configured to readout and, in some embodiment, magnify measurements by the BioFETs 110 and/or the temperature sensors 112. As should be appreciated, readout of a temperature sensor or BioFET is accomplished by measuring a conductance or resistance of the temperature sensor or the BioFET since the conductance or resistance varies based on temperature or the presence and/or concentration of bio-entities.

Figure 7A:
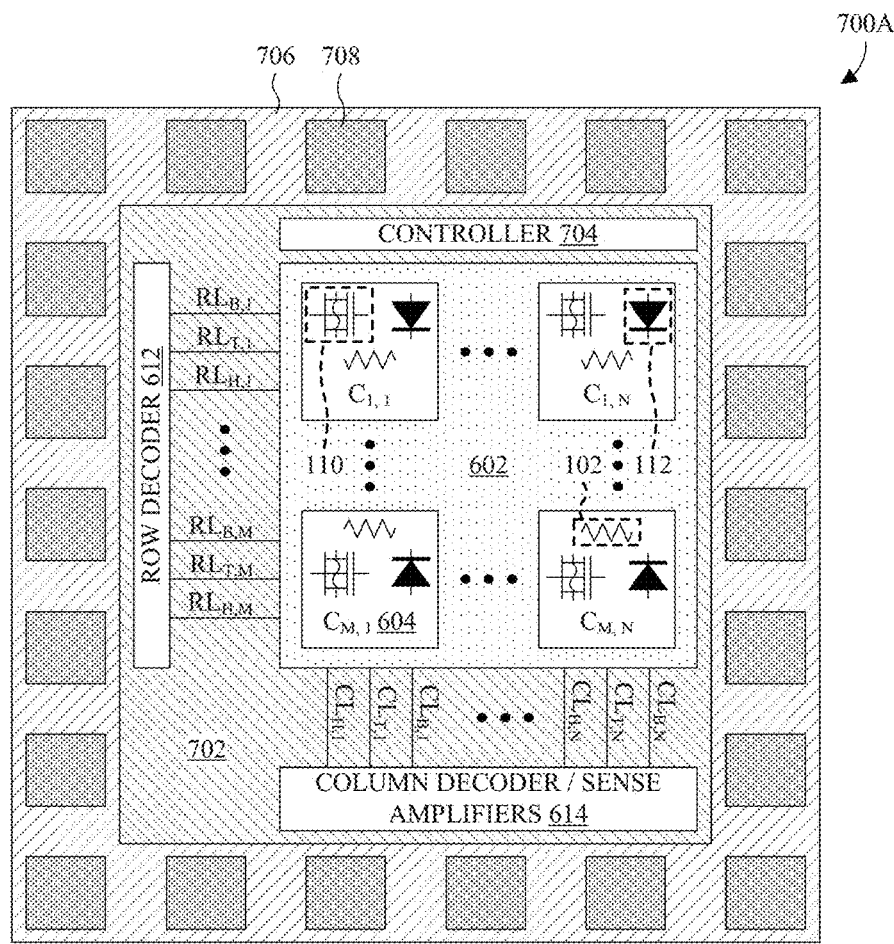
FIG. 7A illustrates a layout view of some embodiments of the biosensor of FIG. 6.

With reference to FIG. 7A, a layout view 700A of some embodiments of the biosensor of FIG. 6 is provided. As illustrated, the unit cells 604 of the array 602 are arranged in rows and columns and laterally surrounded by peripheral circuitry 702. The peripheral circuitry 702 comprises the row decoder 612 and the column decoder/sense amplifier 614, as well as a controller 704. The controller 704 is configured to control the heaters 102 of the unit cells 604 to maintain overlying fluid at target temperatures to facilitate biosensing. For example, the controller 704 may control the heaters 102 to facilitate thermal cycling during PCR. Further, in some embodiments, the controller 704 controls the heaters 102 based on feedback from the temperature sensors 112. The controller 704 may be, for example, a microcontroller or an electronic processor configured to control the heaters 102.

A substrate 706 supports the peripheral circuitry 702 and the array 602 of unit cells 604. Further, in some embodiments, the substrate 706 supports bond pads 708. The bond pads 708 are laterally spaced along a periphery of the peripheral circuitry 702 to provide electrical coupling between the biosensor and external devices. In some embodiments, the bond pads 708 laterally enclose the peripheral circuitry 702, and/or are electrically coupled to the peripheral circuitry 702 and/or the array 602 of unit cells 604 by a BEOL interconnect structure. Further, in some embodiments, the bond pads 708 are as described with regard to the pad openings 320 and the line or pad features 306 of FIGS. 3A and 3B. Even more, in some embodiments, the bond pads 708 are electrically coupled to the BEOL interconnect structure by through substrate vias (TSVs). For example, the substrate 706 may include the carrier substrate 108 of FIGS. 3A and 3B and the BEOL interconnect structure 106 of FIGS. 3A and 3B, such that the bond pads 708 may be arranged under the carrier substrate 108 and electrically coupled to line or pad features 306 of FIGS. 3A and 3B by through substrate vias (TSVs) extending through the carrier substrate 108 to the line or pad features 306.

Figure 7B:
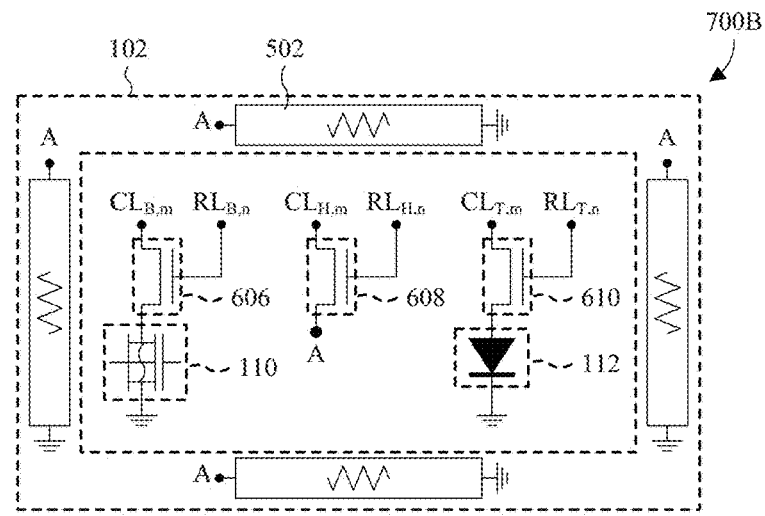
FIG. 7B illustrates a layout view of some embodiments of a unit cell in the biosensor of FIG. 7A.

With reference to FIG. 7B, a layout view 700B of some embodiments of a unit cell 604 of FIG. 7A is provided. As illustrated, a BioFET 110 is electrically coupled in series with a BioFET access transistor 606 and, in some embodiments, a temperature sensor 112 is electrically coupled in series with a temperature access transistor 610. Further, a heater 102 is electrically coupled in series with a heater access transistor 608 and is arranged along a periphery of the BioFET 110, the temperature sensor 112, the access transistors 606, 608, 610, or a combination of the foregoing. The heater 102 comprises a plurality of heating segments 502 laterally spaced along the periphery. In some embodiments, the heating segments 502 are electrically coupled in parallel, and/or laterally enclose the BioFET 110, the temperature sensor 112, and the access transistors 606, 608, 610.

While FIGS. 6, 7A, and 7B illustrate the temperature sensors 112 as diodes, other configurations of the temperature sensors 112 are amenable in other embodiments. For example, the temperature sensors 112 may take on one of the configuration of FIGS. 4C-F. Further, while the unit cells 604 are illustrated as each having a heater, neighboring unit cells may share a heater in other embodiments. For example, the unit cells 604 may be grouped into multiple groups each having multiple unit cells that share a heater. As another example, the unit cells 604 may be divided into 2×2 blocks of unit cells that each has a large heater. Even more, while the unit cells 604 are illustrated as each having a temperature sensor, the temperature sensors 112 may be omitted in other embodiments and/or only some, but not all, of the unit cells 604 may have individual temperature sensors in other embodiments.

Moreover, in other embodiments of FIGS. 6, 7A, and 7B, there may be a one-to-many correspondence between the heaters 102 and the temperature sensors 112, such that the heaters 102 are controlled based on feedback from the corresponding temperature sensors 112. For example, the unit cells 604 may be divided into blocks of unit cells, each block having multiple unit cells. The blocks may, for example, share a common size and/or may, for example, be 2×2, 3×3, or 4×4 blocks of unit cells. Further, each block may comprise X heaters and Y temperature sensors, where Y is greater than X. For example, each block may comprise 1 heater and about 2-5 temperatures sensors. The locations of the heaters 102 and the temperature sensors 112 may, for example, be determined based on a temperature uniformity simulation.

With reference to FIGS. 8A-8E, 9A-9F, and 10-13, a series of cross-sectional views 800A-800E, 900A-900F, 1000-1300 of some embodiments of a method for manufacturing a biosensor with a BioFET and a heater is provided. The biosensor may, for example, be configured as described with regards to FIG. 3A or 3B. Further, FIGS. 9A-9F may be, for example, alternatives to FIGS. 8A-8E.

Figure 8A:
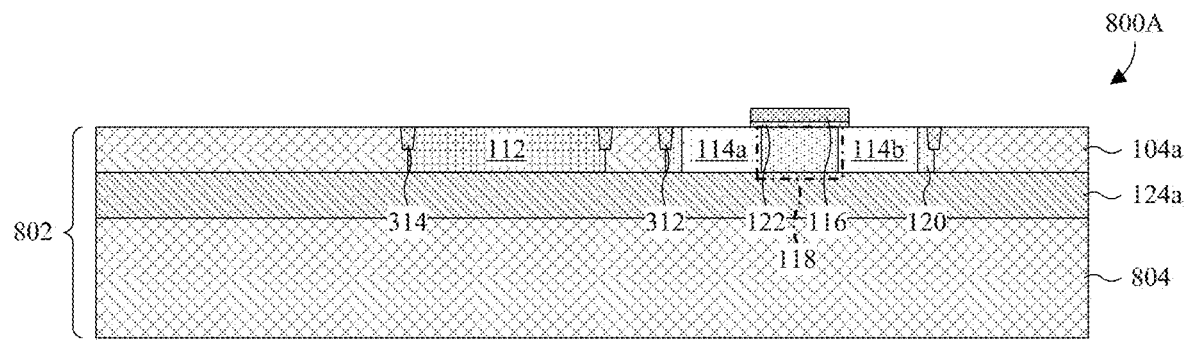
FIGS. 8A-8E, 9A-9F, and 10-13 illustrate a series of cross-sectional views of some embodiments of a method for manufacturing a biosensor with a BioFET and a heater.

As illustrated by the cross-sectional view 800A of FIG. 8A, an SOI substrate 802 is provided. The SOI substrate 802 comprises a bulk semiconductor substrate 804 over which a dielectric layer 124a and a semiconductor layer 104a are stacked. As seen hereafter, the bulk semiconductor substrate 804 is sacrificial. The bulk semiconductor substrate 804 and the semiconductor layer 104a may be, for example, monocrystalline silicon, and/or the dielectric layer 124a may be, for example, silicon dioxide.

A pair of source/drain regions 114a, 114b is formed in the semiconductor layer 104a, such that the source/drain regions 114a, 114b are laterally spaced from one another. For example, ions may be implanted into the semiconductor layer 104a to form the source/drain regions 114a, 114b in the semiconductor layer 104a. The source/drain regions 114a, 114b are formed with a first doping type and are formed in a region of the semiconductor layer 104a that has a second doping type opposite the first doping type, such that a channel region 118 is formed in the semiconductor layer 104a between the source/drain regions 114a, 114b. In some embodiments, the region within which the source/drain regions 114a, 114b are formed is a bulk of the semiconductor layer 104a, such that the semiconductor layer 104a has the second doping type. In other embodiments, the region within which the source/drain regions 114a, 114b are formed is a well region 120 of the semiconductor layer 104a. The well region 120 may be formed before the source/drain regions 114a, 114b by, for example, ion implantation.

In some embodiments, a gate electrode 116 and a gate dielectric layer 122 are formed stacked over the channel region 118, laterally between the source/drain regions 114a, 114b. In some embodiments, the process for forming the gate electrode 116 and the gate dielectric layer 122 comprises sequentially depositing or growing a dielectric layer and a conductive layer stacked over the semiconductor layer 104a. For example, the dielectric and conductive layers may be deposited or grown by, for example, thermal oxidation, electro chemical plating (ECP), vapor deposition, sputtering, or a combination of the foregoing. Further, in some embodiments, the process comprises patterning the dielectric and conductive layers using, for example, photolithography to selectively etch the dielectric and conductive layers respectively into the gate dielectric layer 122 and the gate electrode 116.

Also, in some embodiments, a temperature sensor 112 is formed in the semiconductor layer 104a or over the semiconductor layer 104a. As to the former, for example, an n-type doped region and a p-type doped region may be formed in the semiconductor layer 104a to define a temperature diode. As to the latter, for example, a layer of temperature sensitive material may be deposited or grown over the semiconductor layer 104a, and subsequently patterned using photolithography to selectively etch the layer into the temperature sensor 112. The temperature sensitive material is a material, such as doped polysilicon, with a resistance that varies predictably with temperature.

Also, in some embodiments, a first isolation region 312 and/or a second isolation region 314 are formed in the semiconductor layer 104a. In some embodiments, the first and/or second isolation regions 312, 314 extend entirely through the semiconductor layer 104a, and/or are STI regions. Further, in some embodiments, the first isolation region 312 extends laterally to enclose the source/drain regions 114a, 114b, and/or the second isolation region 314 extends laterally to enclose the temperature sensor 112. The process for forming the first and/or second isolation regions 312, 314 may comprise, for example, performing an etch into the semiconductor layer 104a to define one or more trenches corresponding the first and/or second isolation regions 312, 314, and subsequently depositing or growing a dielectric material filling the one or more trenches.

Figure 8B:
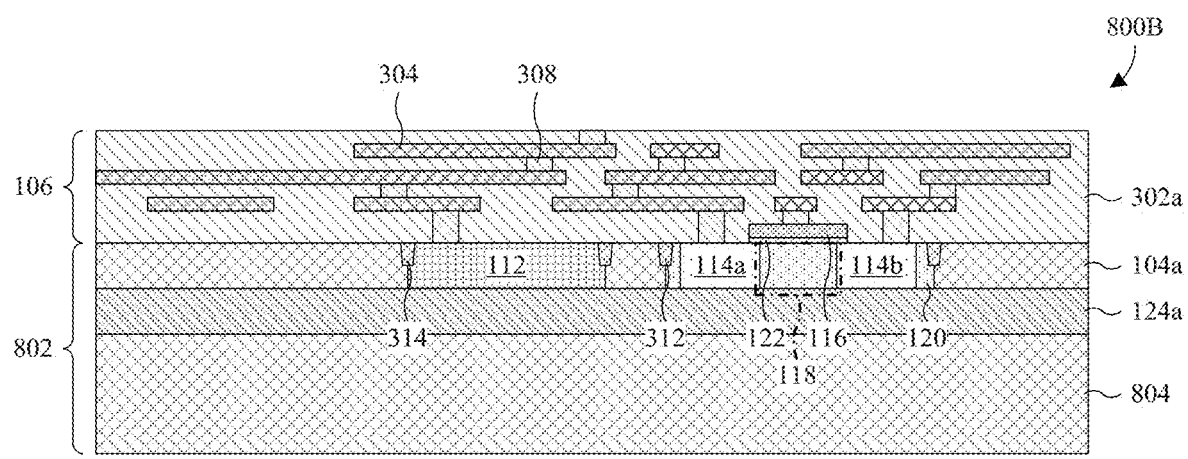

As illustrated by the cross-sectional view 800B of FIG. 8B, a BEOL interconnect structure 106 is partially formed over the SOI substrate 802. The BEOL interconnect structure 106 is formed with first interconnect layers 304 of line or pad features and second interconnect layers 308 of via features alternatingly stacked within a lower ILD layer 302a. The first and second interconnect layers 304, 308 may be, for example, formed by a single-damascene-like process or a dual-damascene-like process. A single-damascene-like or dual-damascene-like process is a single-damascene or dual-damascene process that is not restricted to copper.

Figure 8C:
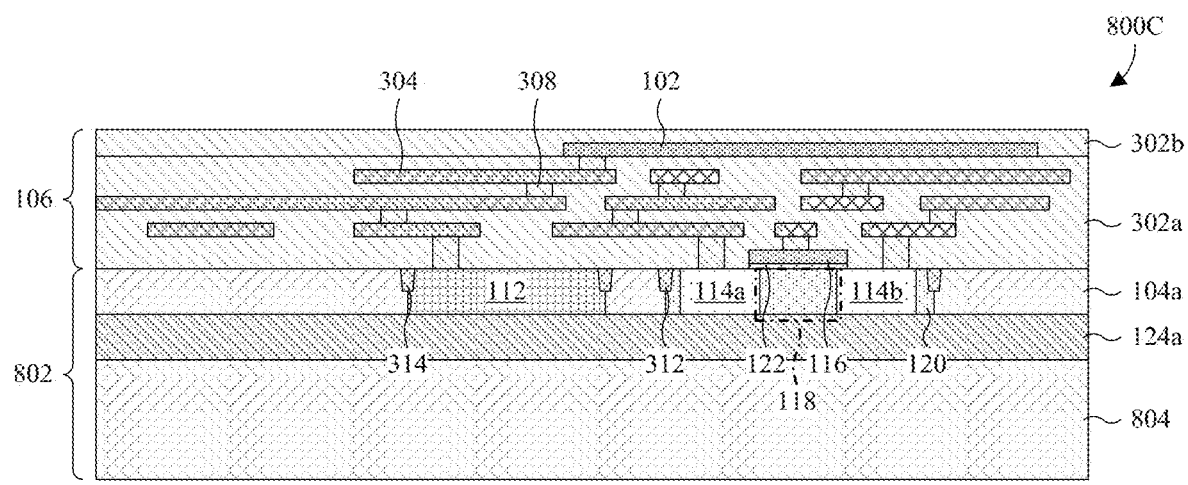

As illustrated by the cross-sectional view 800C of FIG. 8C, a heater 102 is formed over the lower ILD layer 302a, and an upper ILD layer 302b is formed covering the heater 102, to complete the BEOL interconnect structure 106. In some embodiments, the process for forming the heater 102 comprises depositing or growing a conductive layer, and subsequently patterning the conductive layer into the heater 102 using photolithography to selectively etch the conductive layer. The conductive layer may, for example, be patterned according to one of the layouts described in FIGS. 5A-5F. Further, in some embodiments, the process for forming the upper ILD layer 302b comprises depositing or growing the upper ILD layer 302b, and subsequently performing a planarization into an upper or top surface of the upper ILD layer 302b. The upper ILD layer 302b may be deposited or grown by, for example, thermal oxidation, vapor deposition, sputtering, or a combination of the foregoing. The planarization may be performed by, for example, chemical mechanical polishing (CMP).

Figure 8D:
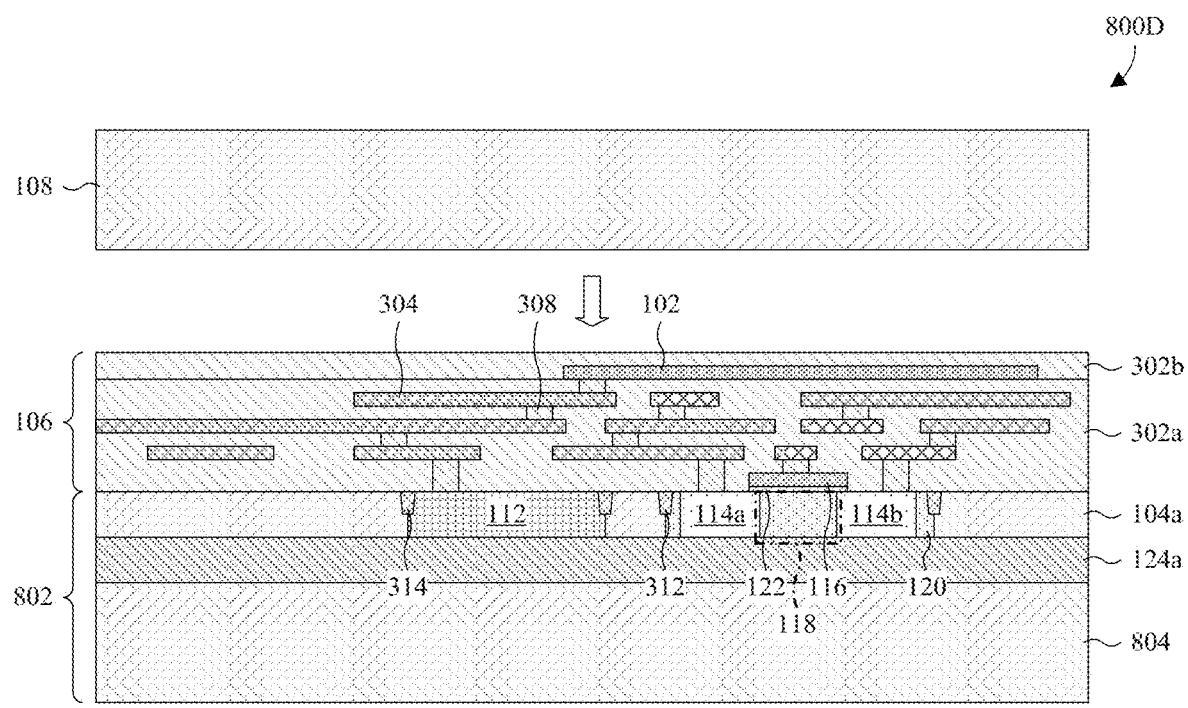

As illustrated by the cross-sectional view 800D of FIG. 8D, a carrier substrate 108 is bonded to the SOI substrate 802 through the BEOL interconnect structure 106. For example, the carrier substrate 108 may be bonded to the BEOL interconnect structure 106 by a fusion bonding process, such as a hydrophilic fusion bonding process.

Figure 8E:
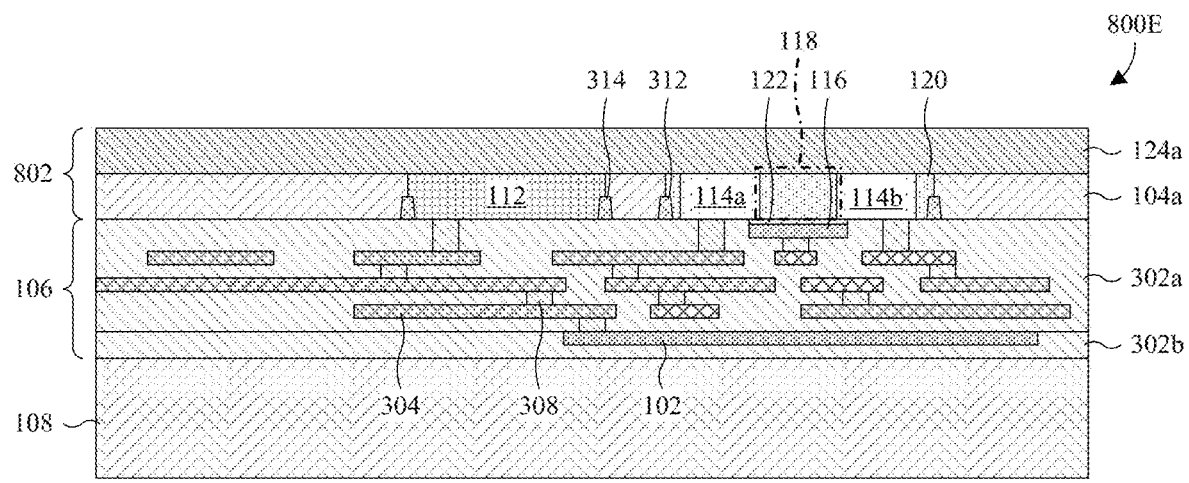

As illustrated by the cross-sectional view 800E of FIG. 8E, the structure of FIG. 8D is flipped vertically and the SOI substrate 802 is thinned to remove the bulk semiconductor substrate 804 (see, e.g., FIG. 8D). In some embodiments, the bulk semiconductor substrate 804 is removed by grinding, CMP, etching back, or a combination of the foregoing.

Figure 9A:
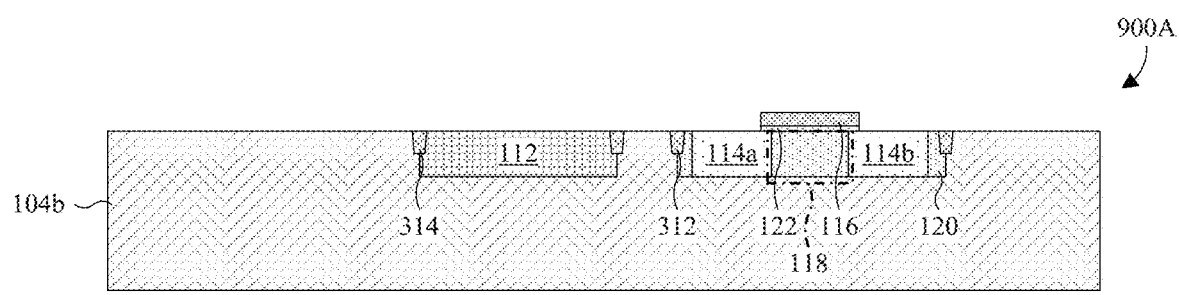

As illustrated by the cross-sectional view 900A of FIG. 9A, a variant of FIG. 8A is provided in which a bulk semiconductor substrate 104b is used in place of the SOI substrate 802 of FIGS. 8A-8E. The bulk semiconductor substrate 104b may, for example, be a bulk substrate of monocrystalline silicon, an epitaxial wafer, or some other bulk semiconductor substrate.

Figure 9B:
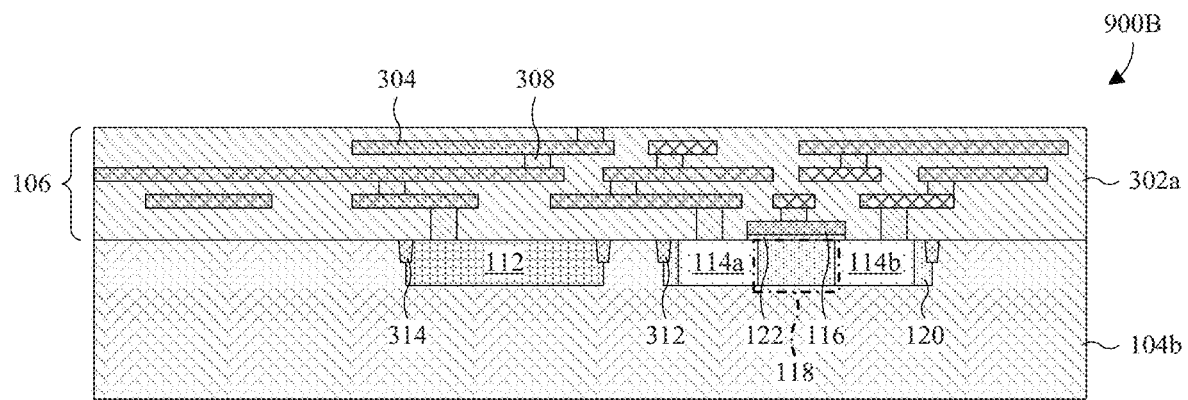
Figure 9C:
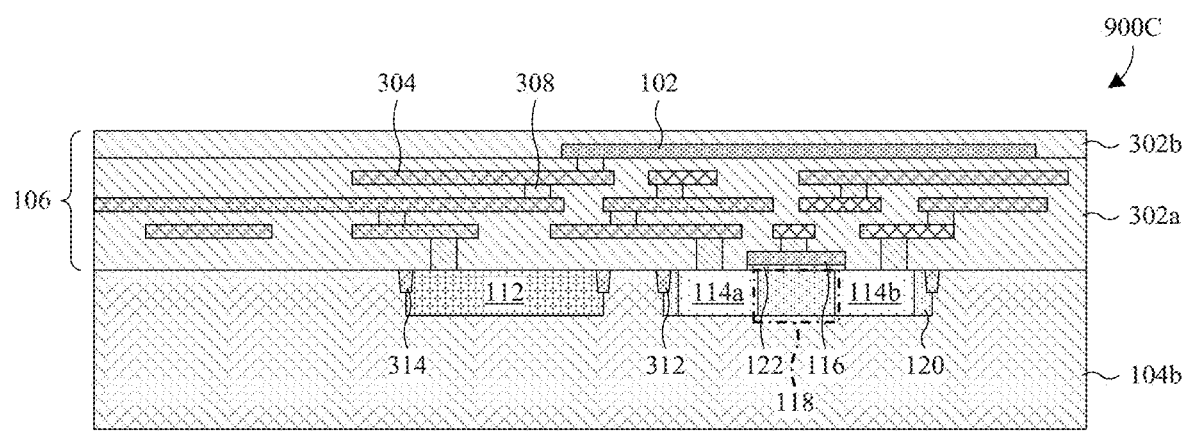

As illustrated by the cross-sectional views 900B, 900C of FIGS. 9B and 9C, variants respectively of FIGS. 8B and 8C are provided in which a BEOL interconnect structure 106 is formed over the bulk semiconductor substrate 104b. The BEOL interconnect structure 106 is formed with first interconnect layers 304 of line or pad features and second interconnect layers 308 of via features are alternatingly stacked within ILD layers 302a, 302b. Further, the BEOL interconnect structure 106 is formed with a heater 102 embedded in the ILD layers 302a, 302b and, in some embodiments, covering the channel region 118.

Figure 9D:
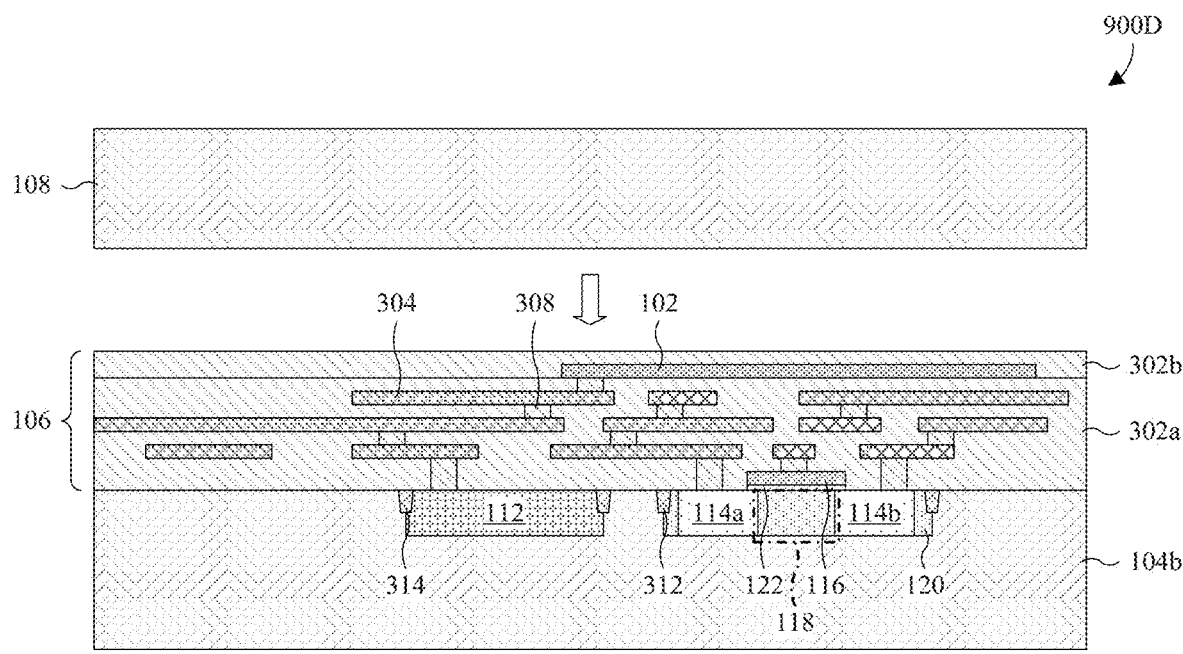

As illustrated by the cross-sectional view 900D of FIG. 9D, a carrier substrate 108 is bonded to the bulk semiconductor substrate 104b through the BEOL interconnect structure 106. For example, the carrier substrate 108 may be bonded to the BEOL interconnect structure 106 by a fusion bonding process, such as a hydrophilic fusion bonding process.

Figure 9E:
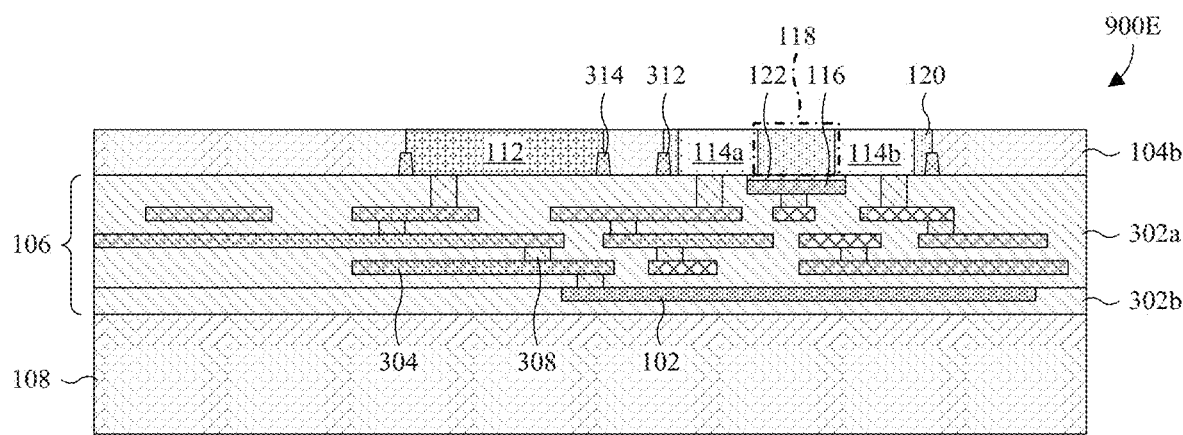

As illustrated by the cross-sectional view 900E of FIG. 9E, the structure of FIG. 9D is flipped vertically and the bulk semiconductor substrate 104b is thinned to expose the channel region 118 and the source/drain regions 114a, 114b. In some embodiments, the bulk semiconductor substrate 104b is thinned by grinding, CMP, high selectivity etching back, or a combination of the foregoing.

Figure 9F:
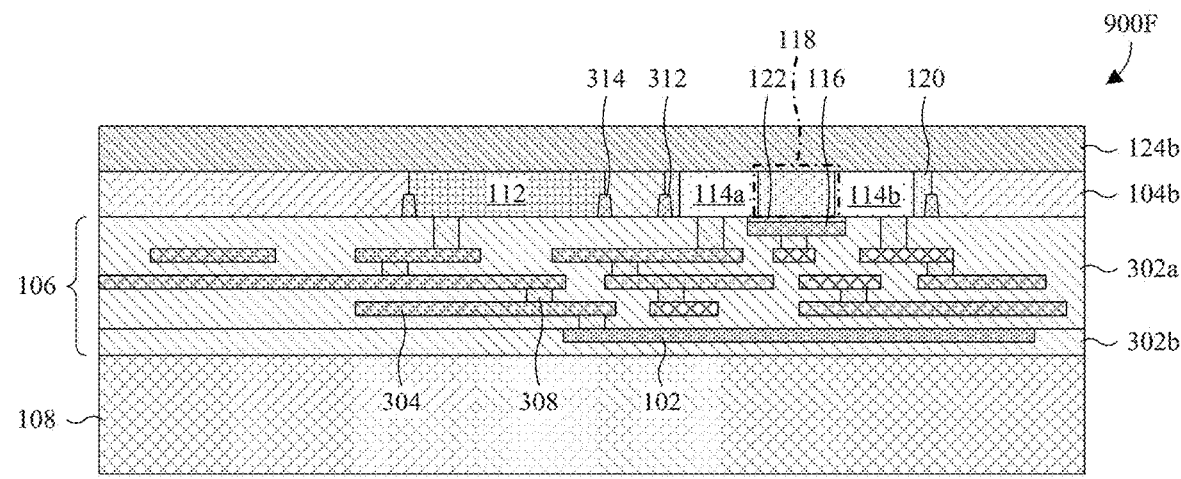

As illustrated by the cross-sectional view 900F of FIG. 9F, a dielectric layer 124b is formed over the bulk semiconductor substrate 104b. In some embodiments, the dielectric layer 124b is formed of, for example, silicon dioxide, silicon nitride, or a combination of the foregoing. Further, in some embodiments, the process for forming the dielectric layer 124b comprises depositing or growing the dielectric layer 124b. The dielectric layer 124b may be deposited or grown by, for example, thermal oxidation, vapor deposition, sputtering, or a combination of the foregoing.

Figure 10:
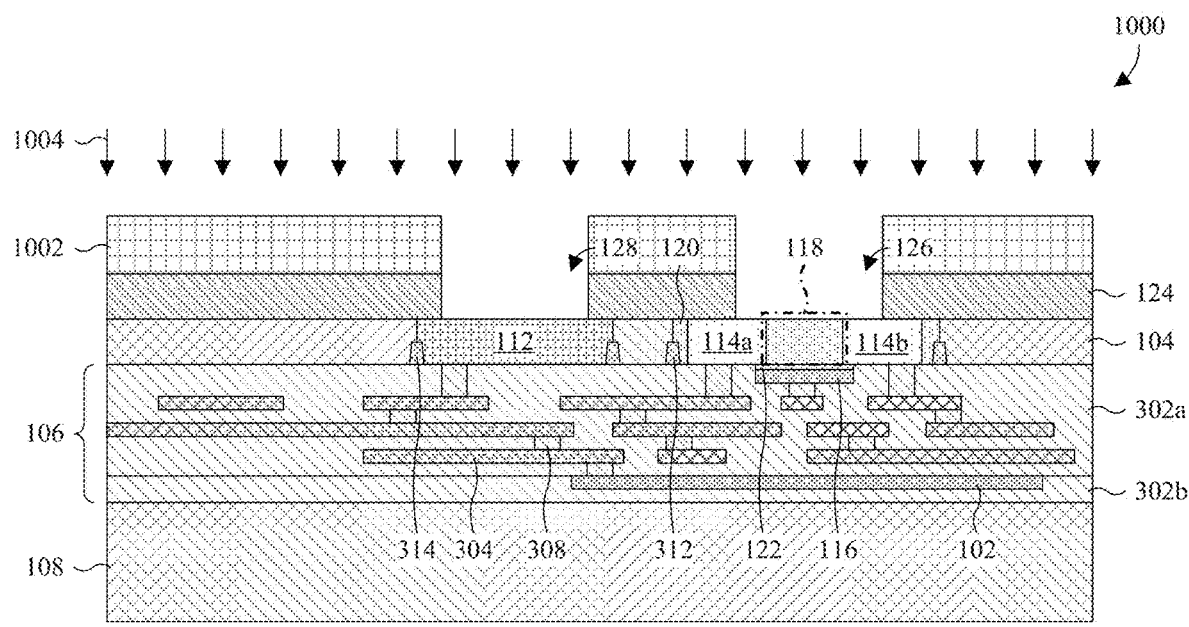

As illustrated by the cross-sectional view 1000 of FIG. 10, a first etch is performed into a passivation layer 124 to form a sensing well 126 laterally between the source/drain regions 114a, 114b and, in some embodiments, exposing the channel region 118. Further, in some embodiments, the first etch is performed into the passivation layer 124 to form a heating well 128 directly over a temperature sensor 112 and laterally spaced from the sensing well 126. The passivation layer 124 and the semiconductor substrate 104 may, for example, respectively be the dielectric layer 124a of FIG. 8E and the semiconductor layer 104a of FIG. 8E, such that FIG. 10 may proceed from FIG. 8E. Alternatively, the passivation layer 124 and the semiconductor substrate 104 may, for example, respectively be the dielectric layer 124b of FIG. 9F and the bulk semiconductor substrate 104b of FIG. 9F, such that FIG. 10 may proceed from FIG. 9F.

The process for performing the first etch may comprise, for example, depositing or growing a first photoresist layer 1002 over the passivation layer 124. Further, the process may comprise, for example, patterning the first photoresist layer 1002 using photolithography, such that the first photoresist layer 1002 comprises one or more openings corresponding to the sensing well 126 and/or the heating well 128. With the first photoresist layer 1002 patterned, the process may comprise, for example, applying one or more first etchants 1004 to the passivation layer 124 with the first photoresist layer 1002 in place, and subsequently stripping the first photoresist layer 1002.

Figure 11:
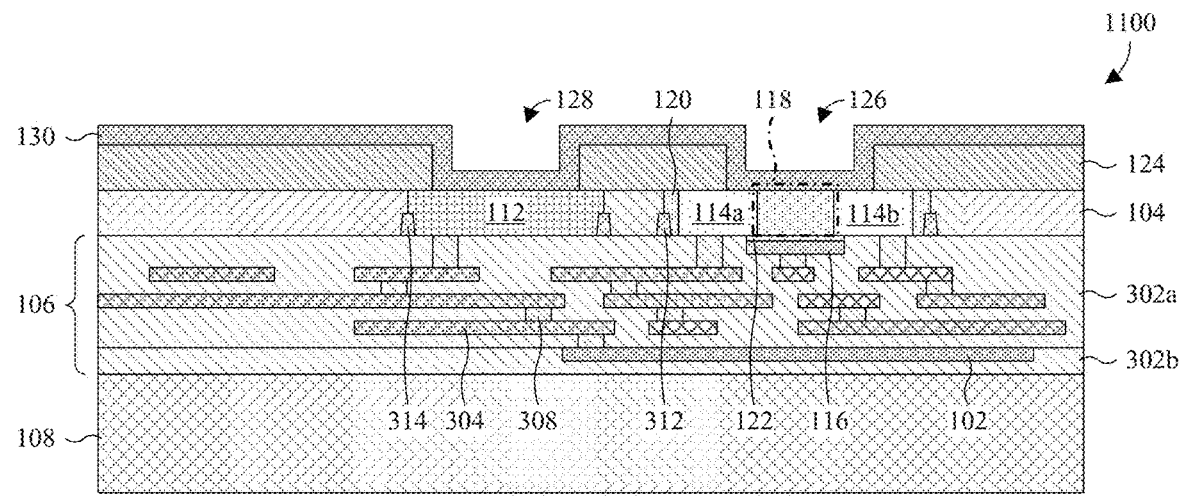

As illustrated by the cross-sectional view 1100 of FIG. 11, a biosensing layer 130 is formed lining the sensing well 126. In some embodiments, the biosensing layer 130 is also formed covering the passivation layer 124 and/or lining the heating well 128. Further, in some embodiments, the biosensing layer 130 is formed conformally, and/or is formed of titanium nitride, titanium, a high κ dielectric, or a combination of the foregoing. The process for forming the biosensing layer 130 may comprise depositing or growing the biosensing layer 130 covering the passivation layer 124 and lining the sensing well 126. The biosensing layer 130 may be deposited or grown by, for example, vapor deposition, sputtering, atomic layer deposition (ALD), or a combination of the foregoing.

Figure 12:
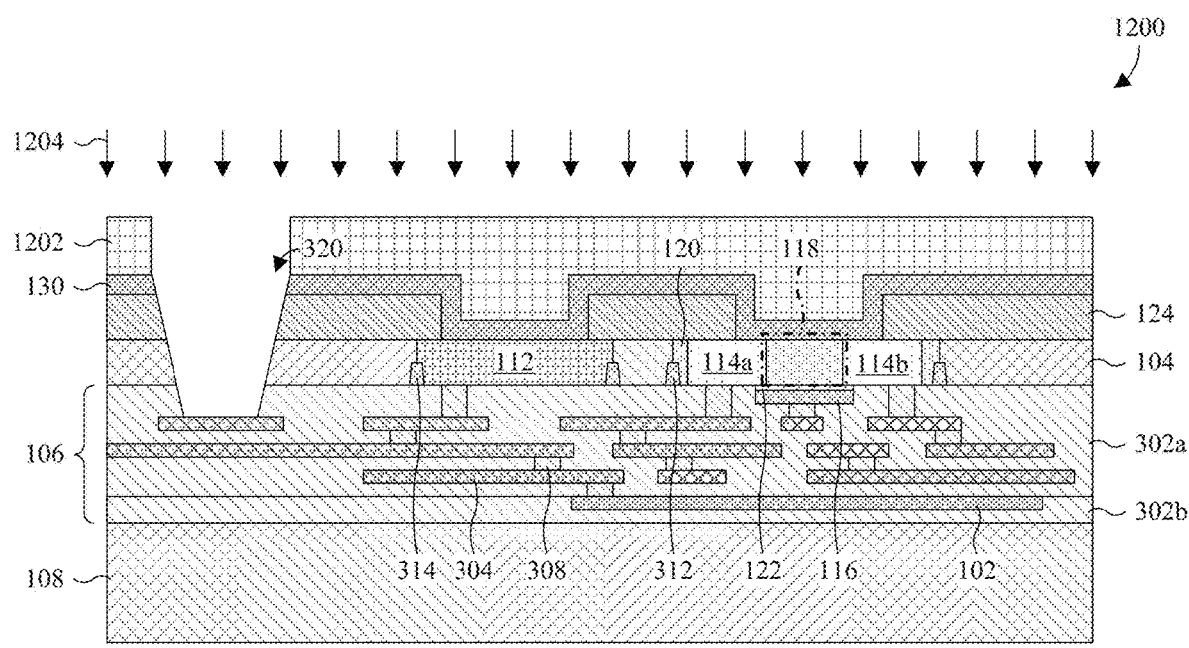

As illustrated by the cross-sectional view 1200 of FIG. 12, in some embodiments, a second etch is performed into the passivation layer 124, the semiconductor substrate 104, and the ILD layer 302 to form a pad opening 320 exposing one of the first interconnect layers 304 of the BEOL interconnect structure 106. Further, in some embodiments, the second etch is performed through the biosensing layer 130, and/or is formed along the periphery of the semiconductor substrate 104 and the BEOL interconnect structure 106.

The process for performing the second etch may comprise, for example, depositing or growing a second photoresist layer 1202 over the passivation layer 124 and/or the biosensing layer 130. Further, the process may comprise, for example, patterning the second photoresist layer 1202 using photolithography, such that the second photoresist layer 1202 comprises an opening corresponding to the pad opening 320. With the second photoresist layer 1202 patterned, the process may comprise, for example, applying one or more second etchants 1204 to the passivation layer 124, the semiconductor substrate 104, and the ILD layer 302 with the second photoresist layer 1202 in place, and subsequently stripping the second photoresist layer 1202.

Figure 13:
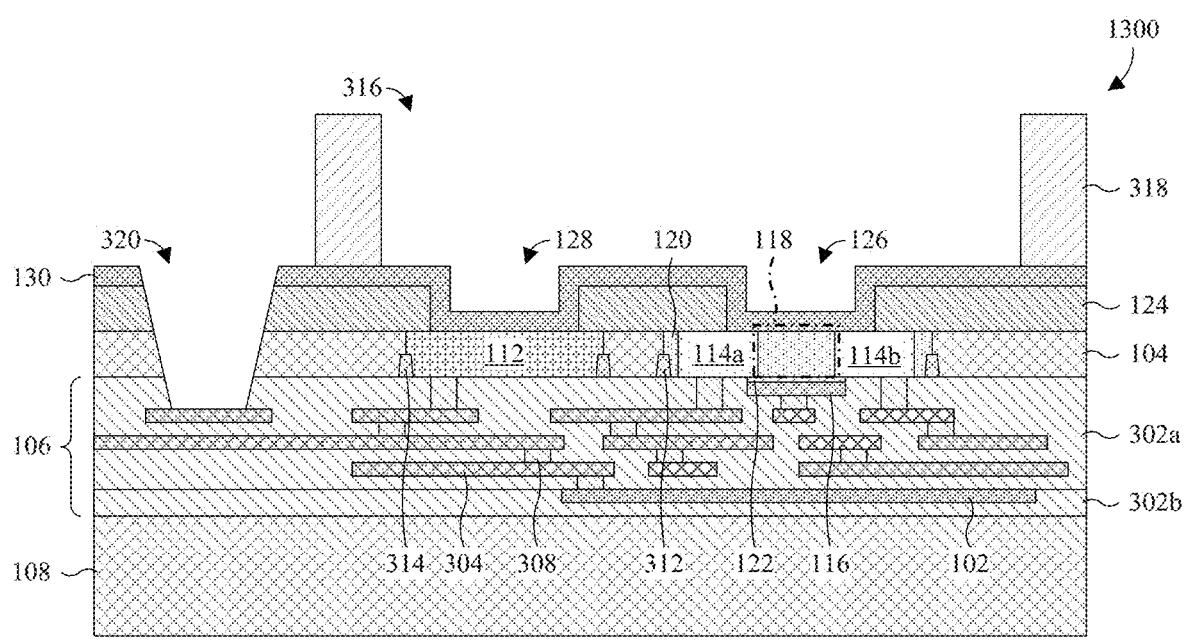

As illustrated by the cross-sectional view 1300 of FIG. 13, a channel structure 318 is formed over the passivation layer 124 and, in some embodiments, the biosensing layer 130 to define a fluidic channel 316 over the sensing well 126. The channel structure 318 may, for example, be formed, such that the fluidic channel 316 is covered or exposed to a surrounding environment of the biosensor. Further, the channel structure 318 may, for example, be formed with a microelectromechanical systems (MEMS) device to control the flow and/or circulation of fluid through the fluidic channel 316.

Figure 14:
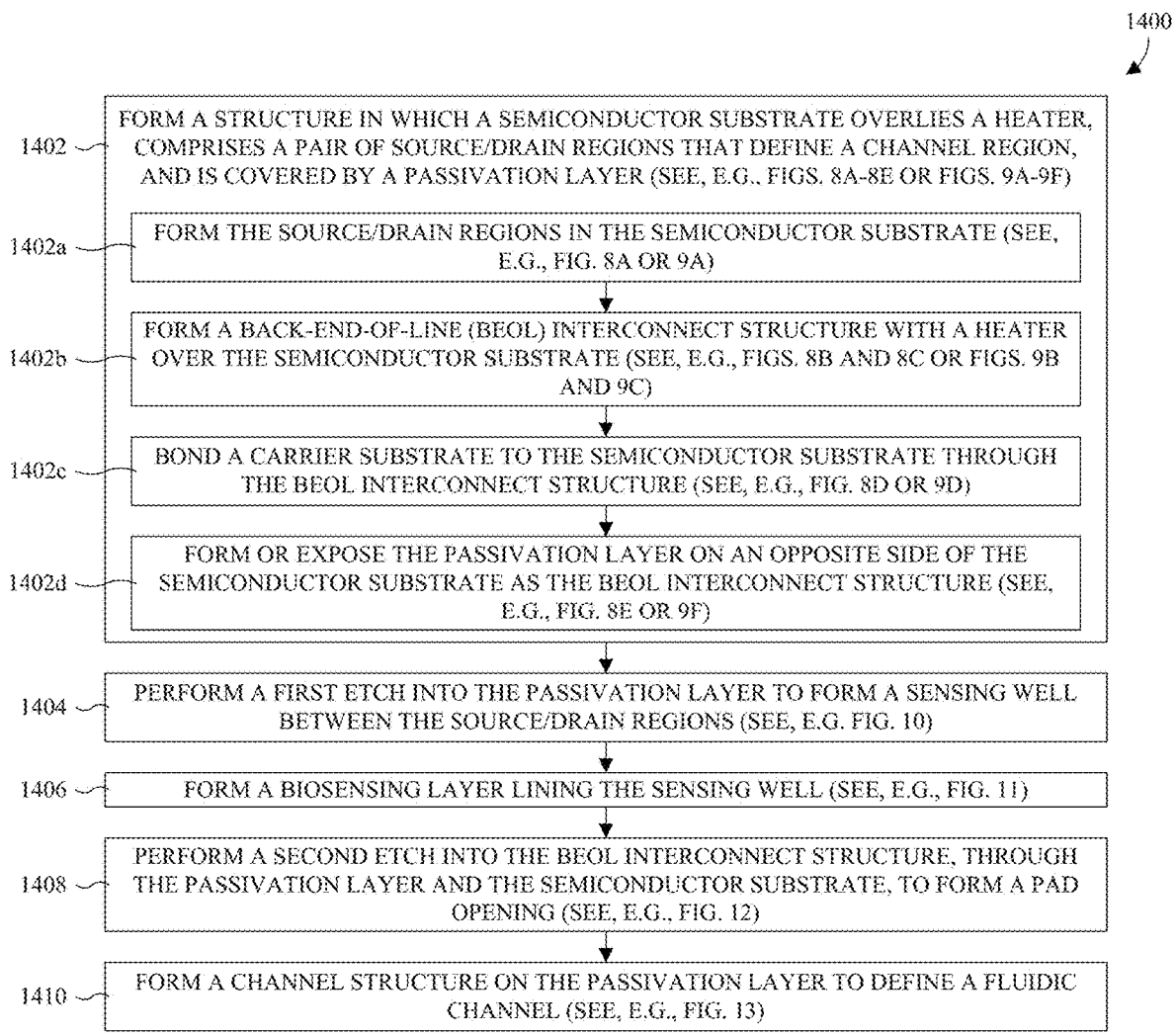
FIG. 14 illustrates a flowchart of some embodiments of the method of FIGS. 8A-8E, 9A-9F, and 10-13.

With reference to FIG. 14, a flowchart 1400 of some embodiments of the method of FIGS. 8A-8E, 9A-9F, and 10-13 is provided.

At 1402, a structure is formed in which a semiconductor substrate overlies a heater, comprises a pair of source/drain regions that define a channel region, and is covered by a passivation layer. See, for example, FIGS. 8A-8E or FIGS. 9A-9F.

At 1402a, the source/drain regions are formed in the semiconductor substrate. In some embodiments, a temperature sensor is also formed in or over the semiconductor substrate, laterally adjacent to the source/drain regions. See, for example, FIG. 8A or 9A.

At 1402b, a BEOL interconnect structure with a heater is formed over the semiconductor substrate. See, for example, FIGS. 8B and 8C or FIGS. 9B and 9C.

At 1402c, a carrier substrate is bonded to the semiconductor substrate through the BEOL interconnect structure. See, for example, FIG. 8D or 9D.

At 1402d, the passivation layer is formed or exposed on an opposite side of the semiconductor substrate as the BEOL interconnect structure. See, for example, FIG. 8E or 9F. In some embodiments, the semiconductor substrate is thinned before forming the passivation layer. See, for example, FIG. 9E.

At 1404, a first etch is performed into the passivation layer to form a sensing well between the source/drain regions. In some embodiments, the second etch is also performed to form a heating well adjacent to the temperature sensor. See, for example, FIG. 10.

At 1406, a biosensing layer is formed lining the sensing well. See, for example, FIG. 11.

At 1408, a second etch is performed into the BEOL interconnect structure, through the passivation layer and the semiconductor substrate, to form a pad opening. In some embodiments, the second etch is also performed through the biosensing layer. See, for example, FIG. 12.

At 1410, a channel structure is formed on the passivation layer to define a fluidic channel. See, for example, FIG. 13.

While the method described by the flowchart 1400 is illustrated and described herein as a series of acts or events, it will be appreciated that the illustrated ordering of such acts or events are not to be interpreted in a limiting sense. For example, some acts may occur in different orders and/or concurrently with other acts or events apart from those illustrated and/or described herein. Further, not all illustrated acts may be required to implement one or more aspects or embodiments of the description herein, and one or more of the acts depicted herein may be carried out in one or more separate acts and/or phases.

In view of the foregoing, in some embodiments, the present disclosure provides a biosensor. A semiconductor substrate comprises a source region and a drain region. A heater is under the semiconductor substrate. A sensing well is over the semiconductor substrate, laterally between the source region and the drain region. A sensing layer lines the sensing well.

In other embodiments, the present disclosure provides a method for manufacturing a biosensor. A pair of source/drain regions is formed in a semiconductor substrate. A BEOL interconnect structure is formed on a first side of the semiconductor substrate. The BEOL interconnect structure is formed with a heater. A sensing well is formed between the source/drain regions and on a second side of the semiconductor substrate, opposite the first side of the semiconductor substrate. A sensing layer is formed lining the sensing well.

In yet other embodiments, the present disclosure provides another biosensor. A semiconductor substrate comprises a source region and a drain region. A passivation layer is over the semiconductor substrate. Further, the passivation layer comprises a sensing well exposing the semiconductor substrate and laterally between the source and drain regions. A sensing layer conformally lines the sensing well. A carrier substrate is under the semiconductor substrate. A BEOL interconnect structure is between the carrier substrate and the semiconductor substrate. Further, the BEOL interconnect structure comprises a heater directly under the sensing well.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A biosensor comprising:
   a semiconductor substrate comprising a source region and a drain region;
   a heater under the semiconductor substrate;
   a sensing well over the semiconductor substrate, on a first side of the semiconductor substrate, wherein the sensing well is laterally between the source region and the drain region, and wherein a bottom surface of the sensing well is defined by semiconductor material of the semiconductor substrate;
   a back-end-of-line (BEOL) interconnect structure under the semiconductor substrate, on a second side of the semiconductor substrate opposite the first side, wherein the BEOL interconnect structure comprises a plurality of conductive lines and a plurality of conductive vias, wherein the conductive vias and the conductive lines are alternatingly stacked, and wherein one of the conductive vias extends from contact with the source or drain region to contact with one of the conductive lines;
   a sensing layer lining the sensing well, wherein the sensing layer is over and contacts the semiconductor material at the bottom surface of the sensing well; and
   wherein the semiconductor substrate and the sensing layer partially define a pad opening extending through the semiconductor substrate and the sensing layer to another one of the conductive lines, wherein the semiconductor substrate and the sensing layer define a common sidewall in the pad opening, and wherein the semiconductor substrate extends continuously from the common sidewall to the source region.

2. The biosensor according to claim 1, further comprising:
   a passivation layer covering the semiconductor substrate, wherein the passivation layer comprises the sensing well.

3. The biosensor according to claim 2, wherein the sensing well extends through the passivation layer to an upper surface of the semiconductor substrate.

4. The biosensor according to claim 1, wherein the source and drain regions extend from a bottom surface of the semiconductor substrate to a top surface of the semiconductor substrate.

5. The biosensor according to claim 1, further comprising:
   a temperature sensor laterally adjacent to the source and drain regions, wherein the sensing layer is directly over the temperature sensor.

6. The biosensor according to claim 5, wherein the temperature sensor comprises a p-type doped region of the semiconductor substrate and an n-type doped region of the semiconductor substrate, and wherein the p-type and n-type doped regions adjoin to define a PN junction.

7. The biosensor according to claim 5, wherein the temperature sensor comprises a polysilicon layer under the semiconductor substrate.

8. The biosensor according to claim 1, wherein the semiconductor substrate comprises a channel region extending from an interface with the source region to an interface with the drain region, and wherein the biosensor further comprises:
   a gate dielectric layer under and contacting the channel region; and
   a gate electrode under and contacting the gate dielectric layer.

9. The biosensor according to claim 1, wherein the sensing layer extends continuously from the common sidewall to the source region.

10. A biosensor comprising:
    a semiconductor substrate comprising a source region and a drain region;
    a heater under the semiconductor substrate;
    a sensing well over the semiconductor substrate, laterally between the source region and the drain region, wherein the semiconductor substrate is vertically between the heater and the sensing well;
    a sensing layer lining the sensing well;

a temperature sensor laterally adjacent to the source and drain regions; and a heating well directly over the temperature sensor, wherein the heating well is laterally spaced from the sensing well.

11. The biosensor according to claim 10, further comprising:

a back-end-of-line (BEOL) interconnect structure under the semiconductor substrate, wherein the BEOL interconnect structure comprises a plurality of conductive lines and a plurality of conductive vias, wherein the conductive vias and the conductive lines are alternatingly stacked, and wherein one of the conductive vias extends from contact with the source or drain region to contact with one of the conductive lines.

12. The biosensor according to claim 10, wherein the sensing well and the heating well are over the semiconductor substrate on an upper side of the semiconductor substrate, and wherein the temperature sensor and the heater are under the semiconductor substrate on a lower side of the semiconductor substrate that is opposite the upper side.

13. A method for manufacturing a biosensor, the method comprising:

forming a pair of source/drain regions in a semiconductor substrate;

forming a back-end-of-line (BEOL) interconnect structure on a first side of the semiconductor substrate, wherein the BEOL interconnect structure is formed with a heater;

bonding a carrier substrate to the semiconductor substrate through the BEOL interconnect structure;

forming a sensing well between the source/drain regions and on a second side of the semiconductor substrate, opposite the first side of the semiconductor substrate;

forming a temperature sensor laterally adjacent to the source/drain regions; and forming a sensing layer lining the sensing well and further directly over the temperature sensor.

14. The method according to claim 13, further comprising:

providing a semiconductor-on-insulator (SOI) substrate comprising the semiconductor substrate, a sacrificial substrate, and a dielectric layer;

after forming the BEOL interconnect structure, thinning the SOI substrate to remove the sacrificial substrate and to expose the dielectric layer; and forming the sensing well in the dielectric layer.

15. The method according to claim 14, further comprising:

forming the source/drain regions extending through the semiconductor substrate to the dielectric layer.

16. The method according to claim 13, further comprising:

after forming the BEOL interconnect structure, thinning the semiconductor substrate to expose the source/drain regions;

forming a dielectric layer on the second side of the semiconductor substrate; and forming the sensing well in the dielectric layer.

17. The method according to claim 13, wherein forming the temperature sensor comprises:

forming a p-type doped region in the semiconductor substrate; and forming an n-type doped region in the semiconductor substrate, wherein the n-type doped region is formed contacting the p-type doped region to define a PN junction.

18. The method according to claim 13, wherein forming the temperature sensor comprises forming a polysilicon layer on the first side of the semiconductor substrate, and wherein the BEOL interconnect structure is formed covering the polysilicon layer.

19. The method according to claim 13, further comprising:

forming a heating well on the second side of the semiconductor substrate, wherein the heating well is formed aligned to the temperature sensor and spaced from the sensing well.

20. The method according to claim 13, wherein the sensing layer is continuous from a location directly over the temperature sensor to a sidewall of the sensing well that is on an opposite side of the sensing well as the temperature sensor.

* * * * *